US005837812A

United States Patent [19]

Harrison et al.

[11] Patent Number: 5,837,812

[45] Date of Patent: Nov. 17, 1998

[54] HUMAN ISLET, HUMAN BRAIN AND MOUSE BRAIN GLUTAMIC ACID DECARBOXYLASE GAD POLYPEPTIDES

[75] Inventors: Leonard Harrison; Margot Honeyman, both of St. Kilda West; David Cram, Blackburn South; Henry De Aizpurua, Blackburn, all of Australia

[73] Assignee: Amrad Corporation Limited, Richmond, Australia

[21] Appl. No.: 308,952

[22] Filed: Sep. 20, 1994

Related U.S. Application Data

[63] Continuation of Ser. No. 839,805, Feb. 21, 1992, abandoned.

[30] Foreign Application Priority Data

| | | | |
|---|---|---|---|
| Feb. 22, 1991 | [AU] | Australia | PK 4773 |
| Sep. 27, 1991 | [AU] | Australia | PK 8620 |

[51] Int. Cl.[6] .......... C07K 14/435; A61K 39/00

[52] U.S. Cl. .......... 530/350; 424/185.1; 435/69.3; 530/300; 530/395; 536/23.5; 536/23.51

[58] Field of Search .......... 530/300, 350, 530/868; 424/185.1; 536/11, 23.51, 23.5; 435/69.3

[56] References Cited

FOREIGN PATENT DOCUMENTS

| | | |
|---|---|---|
| WO 92/04632 | 9/1991 | WIPO . |
| WO 92/03733 | 3/1992 | WIPO . |
| WO 92/05446 | 4/1992 | WIPO . |

OTHER PUBLICATIONS

Baekkeskov, et al. (Mar. 1987) "Antibodies to a 64,000 $M_r$ Human Islet Cell Antigen Precede the Clinical Onset of Insulin–Dependent Diabetes", *J. Clin. Invest.* 79:926–934.

Baekkeskov, et al. (Sep. 13, 1990) "Identification of the 64K Autoantigen in Insulin–Dependent Diabetes as the GABA–Synthesizing Enzyme Glutamic Acid Decarboxylase", *Nature* 347:151–156.

Bond, et al. (May 1988) "Pattern of Expression of Glutamic Acid Decarboxylae mRNA in the Developing Rat Brain", *Proc. Natl. Acad. Sci. USA* 85:3231–3234.

Chang, et al. (Jun. 1988) "Characterization of the Proteins Purified with Monoclonal Antibodies in Glutamic Acid Decarboxylase", *The Journal of Neuroscience* 8(6):2123–2130.

Erlander, et al. (Jul. 1991) "Two Genes Encode Distinct Glutamate Decarboxylases", *Neuron* 7:91–100.

Jackson, et al. (1990) "Drosophila GABAergic Systems: Sequence and Expression of Glutamic Acid Decarboxylase", *Journal of Neurochemistry* 54(3):1068–1078.

Julien, et al. (1987) "Molecular Cloning, Expression and in situ Hybridization of Rat Brain Glutamic Acid Decarboxylase Messenger RNA", *Neuroscience Letters* 73:173–180.

Julien, et al. (1990) "Rat Brain Glutamic Acid Decarboxylase Sequence Deduced from a Cloned cDNA", *Journal of Neurochemistry* 54(2):703–705.

Katarova, et al. (1990) "Molecular Identification of the 62 kd Form of Glutamic Acid Decarboxylase from the Mouse", *European Journal of Neuroscience* 2(3):190–202.

Kaufman, et al. (May 1986) "Brain Glutamate Decarboxylase Cloned in λ–11: Fusion Protein Produces γ–Aminobutyric Acid", *Science* 232:1138–1140.

Kaufman, et al. (Jan. 1992) "Autoimmunity to Two forms of Glutamate Decarboxylase in Insulin–Dependent Diabetes Mellitus", *J. Clin. Invest.* 89:283–292.

Persson, et al. (Sep. 1990) "Expression of Neurotransmitter–Synthesizing Enzyme Glutamic Acid Decarboxylase in Male Germ Cells", *Molecular and Cellular Biology* 10(9):4701–4711.

Solimena, et al. (May 31, 1990) "Autoantibodies to GABA–ergic Neurons and Pancreatic Beta Cells in Stiff–Man Syndrome", *The New England Journal of Medicine* 322(22):1555–1572.

Wyborski, et al. (1990) "Characterization of a cDNA Coding for Rat Glutamic Acid Decarboxylase", *Molecular Brain Research* 8:193–198.

Cram et al., Biochem. Biophys. Res. Com. 176(3):1239–1244 (May 15, 1991).

Michelsen et al. PNAS. USA 88(19):8754–8758 (Oct. 1991).

Blindermann et al., Eur. J. Biochem. 86:143–152 (1978) in Gottlieb et al., PNAS, USA 83:8808–8812 (Nov. 1986).

Kobayashi et al., J. Neurosci. 7 (9):2768–2772 (1987).

*Primary Examiner*—Thomas M. Cunningham

*Attorney, Agent, or Firm*—Scully, Scott, Murphy & Presser

[57] ABSTRACT

The present invention relates to the identification, cloning and sequencing of nucleic acid molecules encoding an isoform of the enzyme glutamic acid decarboxylase and further relates to the use of these molecules and/or peptides and polypeptides encoded thereby in diagnostic tests for Insulin Dependent Diabetes Mellitus and other diseases in which glutamic acid decarboxylase is an autoantigen and in the treatment of patients suffering from these diseases.

9 Claims, 15 Drawing Sheets

```
                10        20        30        40        50
HBGAD   ATTGCACCCGTGTTTGTTCTCATGGAACAGATTACTCTTAAGAAGATGAG
HIGAD   ATTGCACCCGTGTTTGTTCTCATGGAACAGATTACTCTTAAGAAGATGAG

                60        70        80        90       100
HBGAD   AAAGATCGTTGGATGGTCAAATAAAGATGGTGATGGGTTATTTTCTCCTG
HIGAD   AAAGATCGTTGGATGGTCAAATAAAGATGGTGATGGGTTACTTTCTCCTG

               110       120       130       140       150
HBGAD   GGGGAGCCATATCCAATATGTACAGCACCATGGCTGCTCGTTACAAGTAC
HIGAD   GGGGAGCCATATCCAATATGTACAGCATCATGGCTGCTCGTTACAAGTAC

               160       170       180       190       200
HBGAD   TTCCCAGAAGTGAAGACAAAAGGCATGGCGGCTGTGCCCAAACTGGTCCT
HIGAD   TTCCCAGAAGTGAAGACAAAAGGCATGGCGGCTGTGCCCAAACTGGTCCT

               210       220       230       240       250
HBGAD   CTTCACCTCAGAACACAGTCACTATTCCATAAAGAAAGCCGGGGCTGCGC
HIGAD   CTTCACCTCAGAACACAGTCACTATTCCATAAAGAAAGCCGGGGCTGCGC

               260       270       280       290       300
HBGAD   TTGGCTTTGGAACCGACAATGTGATTTTGATAAAGTGCAATGAAAGGGGG
HIGAD   TTGGCTTTGGAACCGACAATGTGATTTTGATAAAGTGCAATGAAAGGGGG

               310       320       330       340       350
HBGAD   AAGATAATTCCGGCTGATTTAGAGGCAAAAATTCTTGATGCCAAACAAAA
HIGAD   AAGATAATTCCGGCTGATTTAGAGGCAAAAATTCTTGATGCCAAACAAAA
```

FIG.1A

| | 360 370 380 390 400 |
|---|---|
| HBGAD | GGGCTATGTTCCCCTCTATGTCAATGCAACCGCAGGCACGACTGTTTACG |
| HIGAD | GGGCTATGTTCCCCTTTATGTCAATGCAACCGCAGGCACGACTGTTTACG |

| | 410 420 430 440 450 |
|---|---|
| HBGAD | CAGCATTCGATCCAATCCAGGAAATTGCGGACATATGTGAGAAATACAAC |
| HIGAD | GAGCATTCGATCCAATCCAGGAAATTGCGGACATATGTGAGAAATACAAC |

| | 460 470 480 490 500 |
|---|---|
| HBGAD | CTTTGGCTGCATGTGGATGCTGCCTGGGGTGGTGGACTGCTCATGTCCCG |
| HIGAD | CTTTGGCTGCATGTGGATGCTGCCTGGGGTGGTGGACTGCTCATGTCCCG |

| | 510 520 530 540 550 |
|---|---|
| HBGAD | GAAGCACCGCCACAAACTCAGCGGCATAGAAAGGGCCAATTCA |
| HIGAD | GAAGCACCGCCACAAACTCAGCGGCATAGAAAGGGCCAATTCA |

FIG. 1B

```
                                                   **            *
HBGAD   IAPVFVLMEQITLKKMRKIVGWSNKDGDGLFSPGGAISNMYSTMAARYKY
HIGAD   IAPVFVLMEQITLKKMRKIVGWSNKDGDGILSPGGAISNMYSIMAARYKY
FBGAD   IAPVFVLMEQITLKKMREIVGWSSKDGDGIFSPGGAISNMYSIMAARYKF

HBGAD   FPEVKTKGMAAVPKLVLFTSEHSHYSIKKAGAALGFGTDNVILIKCNERG
HIGAD   FPEVKTKGMAAVPKLVLFTSEHSHYSIKKAGAALGFGTDNVILIKCNERG
FBGAD   FPEVKTKGMAAVPKLVLFTSEHSHYSIKKAGAALGFGTDNVILIKCNERG

HBGAD   KIIPADLEAKILDAKQKGYVPLYVNATAGTTVYGAFDPIQEIADICEKYN
HIGAD   KIIPADLEAKILDAKQKGYVPLYVNATAGTTVYGAFDPIQEIADICEKYN
FBGAD   KIIPADLEAKILEAKQKGYVPLYVNATAGTTVYGAFDPIQEIADICEKYN

HBGAD   LWLHVDAAWGGGLLMSRKHRHKLSGIERANS
HIGAD   LWLHVDAAWGGGLLMSRKHRHKLSGIERANS
FBGAD   LWLHVDAAWGGGLLMSRKHRHKLSGIERANS
```

*aa differences between HBGAD and HIGAD

FIG. 2

```
 M  A  S  S  T  P  S  P  A  T  S  S  N  A  G  A  D  P  N  T
ATGGCGTCTTCCACTCCTTCGCCTGCAACCTCCTCGAACGCGGGAGCGGATCCTAATACT   60

 T  N  L  R  P  T  T  Y  D  T  W  C  G  V  A  H  G  C  T  R
ACCAACCTGCGCCCTACAACGTATGATACTTGGTGTGGCGTAGCCCATGGATGCACCAGA  120

 K  L  G  L  K  I  C  G  F  L  Q  R  T  N  S  L  E  E  K  S
AAACTGGGCCTGAAGATCTGTGGCTTCTTACAAAGGACCAATAGCCTGGAAGAGAAGAGT  180

 R  L  V  S  A  F  R  E  R  Q  S  S  K  N  L  L  S  C  E  N
CGTCTTGTGAGCGCCTTCAGGGAGAGGCAGTCCTCCAAGAACCTGCTTTCCTGTGAAAAC  240

 S  D  Q  G  A  R  F  R  R  T  E  T  D  F  S  N  L  F  A  Q
AGTGACCAGGGTGCCCGCTTCCGGCGCACAGAGACCGACTTCTCCAACCTGTTTGCTCAA  300

 D  L  L  P  A  K  N  G  E  E  Q  T  A  Q  F  L  L  E  V  V
GATCTGCTTCCAGCTAAGAACGGGGAGGAGCAAACTGCGCAGTTCTTGCTGGAAGTGGTA  360

 D  I  L  L  N  Y  V  R  K  T  F  D  R  S  T  K  V  L  D  F
GACATACTCCTCAACTATGTCCGCAAGACATTTGATCGCTCCACCAAGGTTCTGGATTTC  420

 H  H  P  H  Q  L  L  E  G  M  E  G  F  N  L  E  L  S  D  H
CACCACCCACACCAGTTGCTGGAAGGCATGGAAGGCTTTAATTTGGAGCTGTCTGACCAC  480

 P  E  S  L  E  Q  I  L  V  D  C  R  D  T  L  K  Y  G  V  R
CCCGAGTCTCTGGAGCAGATCCTGGTTGACTGTAGAGACACCCTGAAGTACGGGGTTCGC  540

 T  G  H  P  R  F  F  N  Q  L  S  T  G  L  D  I  I  G  L  A
ACAGGTCACCCTCGATTTTTCAACCAGCTCTCTACTGGTTTGGATATCATTGGTTTAGCT  600

 G  E  W  L  T  S  T  A  N  T  N  M  F  T  Y  E  I  A  P  V
GGCGAATGGCTGACATCGACTGCCAATACCAATATGTTCACATATGAAATTGCACCCGTG  660

 F  V  L  M  E  Q  I  T  L  K  K  M  R  K  I  V  G  W  S  N
TTTGTTCTCATGGAACAGATTACTCTTAAGAAGATGAGAAAGATCGTTGGATGGTCAAAT  720

 K  D  G  D  G  I  F  S  P  G  G  A  I  S  N  M  Y  S  I  M
AAAGATGGTGATGGGATATTTTCTCCTGGGGGAGCCATATCCAATATGTACAGCATCATG  780

 A  A  R  Y  K  Y  F  P  E  V  K  T  K  G  M  A  A  V  P  K
GCTGCTCGTTACAAGTACTTCCCAGAAGTGAAGACAAAAGGCATGGCGGCTGTGCCCAAA  840

 L  V  L  F  T  S  E  H  S  H  Y  S  I  K  K  A  G  A  A  L
CTGGTCCTCTTCACCTCAGAACACAGTCACTATTCCATAAAGAAAGCCGGGGCTGCGCTT  900

 G  F  G  T  D  N  V  I  L  I  K  C  N  E  R  G  K  I  I  P
GGCTTTGGAACCGACAATGTGATTTTGATAAAGTGCAATGAAAGGGGGAAGATAATTCCG  960

 A  D  L  E  A  K  I  L  D  A  K  Q  K  G  Y  V  P  L  Y  V
GCTGATTTAGAGGCAAAAATTCTTGATGCCAAACAAAAGGGCTATGTTCCCCTTTATGTC 1020
```

FIG.3A

```
 N  A  T  A  G  T  T  V  Y  G  A  F  D  P  I  Q  E  I  A  D
AATGCAACCGCAGGCACGACTGTTTACGGAGCATTCGATCCAATCCAGGAAATTGCGGAC 1080

 I  C  E  K  Y  N  L  W  L  H  V  D  A  A  W  G  G  G  L  L
ATATGTGAGAAATACAACCTTTGGCTGCATGTGGATGCTGCCTGGGGTGGTGGACTGCTC 1140

 M  S  R  K  H  R  H  K  L  S  G  I  E  R  A  N  S  V  T  W
ATGTCCCGGAAGCACCGCCACAAACTCAGCGGCATAGAAAGGGCCAATTCAGTCACCTGG 1200

 N  P  H  K  M  M  G  V  L  L  Q  C  S  A  I  L  V  K  E  K
AACCCTCACAAGATGATGGGCGTGCTGCTCCAGTGCTCTGCCATTCTGGTCAAGGAAAAG 1260

 G  I  L  Q  G  C  N  Q  M  C  A  G  Y  L  F  Q  P  D  K  Q
GGTATACTCCAAGGATGCAACCAGATGTGTGCAGGCTACCTCTTCCAGCCAGACAAGCAG 1320

 Y  D  V  S  Y  D  T  G  D  K  A  I  Q  C  G  R  H  V  D  I
TATGACGTCTCCTATGACACCGGGGACAAGGCGATTCAGTGTGGCCGCCATGTGGACATC 1380

 F  K  F  W  L  M  W  K  A  K  G  T  V  G  F  E  N  Q  I  N
TTCAAGTTCTGGCTGATGTGGAAAGCAAAGGGCACCGTGGGATTTGAAAACCAGATCAAC 1440

 K  C  L  E  L  A  D  Y  L  Y  A  K  I  K  N  R  E  E  P  E
AAATGCCTGGAGCTGGCTGATTACCTCTACGCCAAGATTAAAAACAGAGAAGAGTTTGAG 1500

 M  V  F  D  G  E  P  E  H  T  N  V  C  F  W  Y  I  P  Q  S
ATGGTTTTCGATGGTGAGCCTGAGCACACAAATGTCTGTTTCTGGTACATTCCACAAAGC 1560

 L  R  G  V  P  D  S  P  E  R  R  E  K  L  H  R  V  A  P  K
CTTAGAGGGGTTCCAGATAGCCCTGAGCGACGAGAAAAGCTACACAGGGTGGCTCCCAAG 1620

 I  K  A  L  M  M  E  S  G  T  T  M  V  G  Y  Q  P  Q  G  D
ATCAAAGCTCTGATGATGGAGTCAGGAACAACCATGGTCGGCTACCAGCCTCAAGGGGAC 1680

 K  A  N  F  F  R  N  V  I  S  N  P  A  A  T  Q  S  D  I  D
AAGGCCAACTTCTTCCGGATGGTCATCTCTAACCCAGCCGCCACCCAGTCTGACATCGAT 1740

 F  L  I  E  E  I  E  R  L  G  Q  D  L  *
TTCCTCATTGAGGAGATAGAGAGGTTGGGCCAGGATCTGTAA                   1782
```

FIG.3B

```
 M  A  S  S  T  P  S  P  A  T  S  S  N  A  G  A  D  P  N  T
ATGGCGTCTTCCACTCCTTCGCCTGCAACCTCCTCGAACGCGGGAGCGGATCCTAATACT   60

 T  N  L  R  P  T  T  Y  D  T  W  C  G  V  A  H  G  C  T  R
ACCAACCTGCGCCCTACAACGTATGATACTTGGTGTGGCGTAGCCCATGGATGCACCAGA  120

 K  L  G  L  K  I  C  G  F  L  Q  R  T  N  S  L  E  E  K  S
AAACTGGGCCTGAAGATCTGTGGCTTCTTACAAAGGACCAATAGCCTGGAAGAGAAGAGT  180

 R  L  V  S  A  F  R  E  R  Q  S  S  K  N  L  L  S  C  E  N
CGTCTTGTGAGCGCCTTCAGGGAGAGGCAGTCCTCCAAGAACCTGCTTTCCTGTGAAAAC  240

 S  D  Q  G  A  R  F  R  R  T  E  T  D  F  S  N  L  F  A  Q
AGTGACCAGGGTGCCCGCTTCCGGCGCACAGAGACCGACTTCTCCAACCTGTTTGCTCAA  300

 D  L  L  P  A  K  N  G  E  E  Q  T  A  Q  F  L  L  E  V  V
GATCTGCTTCCAGCTAAGAACGGGGAGGAGCAAACTGCGCAGTTCTTGCTGGAAGTGGTA  360

 D  I  L  L  N  Y  V  R  K  T  F  D  R  S  T  K  V  L  D  F
GACATACTCCTCAACTATGTCCGCAAGACATTTGATCGCTCCACCAAGGTTCTGGATTTC  420

 H  H  P  H  Q  L  L  E  G  M  E  G  F  N  L  E  L  S  D  H
CACCACCCACACCAGTTGCTGGAAGGCATGGAAGGCTTTAATTTGGAGCTGTCTGACCAC  480

 P  E  S  L  E  Q  I  L  V  D  C  R  D  T  L  K  Y  G  V  R
CCCGAGTCTCTGGAGCAGATCCTGGTTGACTGTAGAGACACCCTGAAGTACGGGGTTCGC  540

 T  G  H  P  R  F  F  N  Q  L  S  T  G  L  D  I  I  G  L  A
ACAGGTCACCCTCGATTTTTCAACCAGCTCTCTACTGGTTTGGATATCATTGGTTTAGCT  600

 G  E  W
GGCGAATGG                                                     609
```

FIG.4

```
 G  L  A  G  E  W  L  T  S  T  A  N  T  N  M  F  T  Y  E  I
GGTTTAGCTGGCGAATGGCTGACATCGACTGCCAATACCAATATGTTCACATATGAAATT   651

 A  P  V  F  V  L  M  E  Q  I  T  L  K  K  M  R  K  I  V  G
GCACCCGTGTTTGTTCTCATGGAACAGATTACTCTTAAGAAGATGAGAAAGATCGTTGGA   711

 W  S  N  K  D  G  D  G  I  F  S  P  G  G  A  I  S  N  M  Y
TGGTCAAATAAAGATGGTGATGGATATTTTCTCCTGGGGGAGCCATATCCAATATGTAC   771

 S  I  M  A  A  R  Y  K  Y  F  P  E  V  K  T  K  G  M  A  A
AGCATCATGGCTGCTCGTTACAAGTACTTCCCAGAAGTGAAGACAAAAGGCATGGCGGCT   831

 V  P  K  L  V  L  F  T  S  E  H  S  H  Y  S  I  K  K  A  G
GTGCCCAAACTGGTCCTCTTCACCTCAGAACACAGTCACTATTCCATAAAGAAAGCCGGG   891

 A  A  L  G  F  G  T  D  N  V  I  L  I  K  C  N  E  R  G  K
GCTGCGCTTGGCTTTGGAACCGACAATGTGATTTTGATAAAGTGCAATGAAAGGGGGAAG   951

 I  I  P  A  D  L  E  A  K  I  L  D  A  K  Q  K  G  Y  V  P
ATAATTCCGGCTGATTTAGAGGCAAAAATTCTTGATGCCAAACAAAAGGGCTATGTTCCC  1011

 L  Y  V  N  A  T  A  G  T  T  V  Y  G  A  F  D  P  I  Q  E
CTTTATGTCAATGCAACCGCAGGCACGACTGTTTACGGAGCATTCGATCCAATCCAGGAA  1071

 I  A  D  I  C  E  K  Y  N  L  W  L  H  V  D  A  A  W  G  G
ATTGCGGACATATGTGAGAAATACAACCTTTGGCTGCATGTGGATGCTGCCTGGGGTGGT  1131

 G  L  L  M  S  R  K  H  R  H  K  L  S  G  I  E  R  A  N  S
GGACTGCTCATGTCCCGGAAGCACCGCCACAAACTCAGCGGCATAGAAAGGGCCAATTCA  1191

 V  T  W  N  P  H
GTCACCTGGAACCCTCAC                                            1209
```

FIG.5

```
 G  I  E  R  A  N  S  V  T  W  N  P  H  K  M  M  G  V  L  L
GGCATAGAAAGGGCCAATTCAGTCACCTGGAACCCTCACAAGATGATGGGCGTGCTGCTC 1230

 Q  C  S  A  I  L  V  K  E  K  G  I  L  Q  G  C  N  Q  M  C
CAGTGCTCTGCCATTCTGGTCAAGGAAAAGGGTATACTCCAAGGATGCAACCAGATGTGT 1290

 A  G  Y  L  F  Q  P  D  K  Q  Y  D  V  S  Y  D  T  G  D  K
GCAGGCTACCTCTTCCAGCCAGACAAGCAGTATGACGTCTCCTATGACACCGGGGACAAG 1350

 A  I  Q  C  G  R  H  V  D  I  F  K  F  W  L  M  W  K  A  K
GCGATTCAGTGTGGCCGCCATGTGGACATCTTCAAGTTCTGGCTGATGTGGAAAGCAAAG 1410

 G  T  V  G  F  E  N  Q  I  N  K  C  L  E  L  A  D  Y  L  Y
GGCACCGTGGGATTTGAAAACCAGATCAACAAATGCCTGGAGCTGGCTGATTACCTCTAC 1470

 A  K  I  K  N  R  E  E  F  E  M  V  F  D  G  E  P  E  H  T
GCCAAGATTAAAAACAGAGAAGAGTTTGAGATGGTTTTCGATGGTGAGCCTGAGCACACA 1530

 N  V  C  F  W  Y  I  P  Q  S  L  R  G  V  P  D  S  P  E  R
AATGTCTGTTTCTGGTACATTCCACAAAGCCTTAGAGGGGTTCCAGATAGCCCTGAGCGA 1590

 R  E  K  L  H  R  V  A  P  K  I  K  A  L  M  M  E  S  G  T
CGAGAAAAGCTACACAGGGTGGCTCCCAAGATCAAAGCTCTGATGATGGAGTCAGGAACA 1650

 T  M  V  G  Y  Q  P  Q  G  D  K  A  N  F  F  R  M  V  I  S
ACCATGGTCGGCTACCAGCCTCAAGGGGACAAGGCCAACTTCTTCCGGATGGTCATCTCT 1710

 N  P  A  A  T  Q  S  D  I  D  F  L  I  E  E  I  E  R  L  G
AACCCAGCCGCCACCCAGTCTGACATCGATTTCCTCATTGAGGAGATAGAGAGGTTGGGC 1770

 Q  D  L  *
CAGGATCTGTAA                                                 1782
```

FIG. 6

```
 M  A  S  S  T  P  S  S  S  A  T  S  S  N  A  G  A  D  P  N
ATGGCGTCTTCGACCCCATCTTCGTCCGCAACCTCCTCGAACGCGGGAGCGGACCCCAAT    60

 T  T  N  L  R  P  T  T  Y  D  T  W  C  G  V  A  H  G  C  T
ACCACTAACCTGCGCCCCACAACGTACGATACCTGGTGCGGCGTGGCCCATGGATGCACC   120

 R  K  L  G  L  K  I  C  G  F  L  Q  R  T  N  S  L  E  E  K
AGAAAACTGGGGCTCAAGATCTGCGGCTTCTTGCAAAGGACCAACAGCCTGGAAGAGAAG   180

 S  R  L  V  S  A  F  K  E  R  Q  S  S  K  N  L  L  S  C  E
AGTCGCCTTGTGAGTGCCTTCAAGGAGAGGCAATCCTCCAAGAACCTGCTTTCCTGTGAA   240

 N  S  D  R  D  A  R  F  R  R  T  E  T  D  F  S  N  L  F  A
AACAGCGACCGGGATGCCCGCTTCCGGCGCACAGAGACTGACTTCTCTAATCTGTTTGCT   300

 R  D  L  L  P  A  K  N  G  E  E  Q  T  V  Q  F  L  L  E  V
AGAGATCTGCTTCCGGCTAAGAACGGTGAGGAGCAAACCGTGCAATTCCTCCTGGAAGTG   360

 V  D  I  L  L  N  Y  V  R  K  T  F  D  R  S  T  K  V  L  D
GTGGACATACTCCTCAACTATGTCCGCAAGACATTTGATCGCTCCACCAAGGTGCTGGAC   420

 F  H  H  P  H  Q  L  L  E  G  M  E  G  F  N  L  E  L  S  D
TTTCATCACCCACACCAGTTGCTGGAAGGCATGGAGGGCTTCAACTTGGAGCTCTCTGAC   480

 H  P  E  S  L  E  Q  I  L  V  D  C  R  D  T  L  K  Y  G  V
CACCCCGAGTCCCTGGAGCAGATCCTGGTCGACTGCAGAGACACCTTGAAGTATGGGGTT   540

 R  T  G  H  P  R  F  F  N  Q  L  S  T  G  L  D  I  I  G  L
CGCACAGGTCATCCTCGATTTTTCAACCAGCTCTCCACTGGATTGGATATTATTGGCCTA   600

 A  G  E  W  L  T  S  T  A  N  T  N  M  F  T  Y  E  I  A  P
GCTGGAGAATGGCTGACATCAACGGCCAATACCAACATGTTCACATATGAAATTGCACCA   660

 V  F  V  L  M  E  Q  I  T  L  K  K  M  R  E  I  V  G  W  S
GTGTTTGTCCTCATGGAACAAATAACACTTAAGAAGATGAGAGAGATAGTTGGATGGTCA   720

 S  K  D  G  D  G  I  F  S  P  G  G  A  I  S  N  M  Y  S  I
AGTAAAGATGGTGATGGGATATTTTCTCCTGGGGGCGCCATATCCAACATGTACAGCATC   780

 M  A  A  R  Y  K  Y  F  P  E  V  K  T  K  G  M  A  A  V  P
ATGGCTGCTCGCTACAAGTACTTCCCGGAAGTTAAGACAAAGGGCATGGCGGCTGTGCCT   840

 K  L  V  L  F  T  S  E  Q  S  H  Y  S  I  K  K  A  G  A  A
AAACTGGTCCTCTTCACCTCAGAACAGAGTCACTATTCCATAAAGAAAGCTGGGGCTGCA   900

 L  G  F  G  T  D  N  V  I  L  I  K  C  N  E  R  G  K  I  I
CTTGGCTTTGGAACTGACAATGTGATTTTGATAAAGTGCAATGAAAGGGGGAAAATAATT   960

 P  A  D  F  E  A  K  I  L  E  A  K  Q  K  G  Y  V  P  F  Y
CCAGCTGATTTTGAGGCAAAAATTCTTGAAGCCAAACAGAAGGGATATGTTCCCTTTTAT  1020
```

FIG. 7A

```
 V  N  A  T  A  G  T  T  V  Y  G  A  F  D  P  I  Q  E  I  A
GTCAATGCAACTGCTGGCACGACTGTTTATGGAGCTTTTGATCCGATACAAGAGATTGCA 1080

 D  I  C  E  K  Y  N  L  W  L  H  V  D  A  A  W  G  G  G  L
GATATATGTGAGAAATATAACCTTTGGTTGCATGTCGATGCTGCCTGGGGAGGTGGGCTG 1140

 L  M  S  R  K  H  R  H  K  L  N  G  I  E  R  A  N  S  V  T
CTCATGTCCAGGAAGCACCGCCATAAACTCAACGGCATAGAAAGGGCCAACTCAGTCACC 1200

 N  N  P  H  K  M  M  G  V  L  L  Q  C  S  A  I  L  V  K  E
TGGAACCCTCACAAGATGATGGGCGTGCTGTTGCAGTGCTCTGCCATTCTCGTCAAGGAA 1260

 K  G  I  L  Q  G  C  N  Q  M  C  A  G  Y  L  F  Q  P  D  K
AAGGGTATACTCCAAGGATGCAACCAGATGTGTGCAGGATACCTCTTCCAGCCAGACAAG 1320

 Q  Y  D  V  S  Y  D  T  G  D  K  A  I  Q  C  G  R  M  V  D
CAGTATGATGTCTCCTACGACACCGGGGACAAGGCAATTCAGTGTGGCCGCCACGTGGAT 1380

 I  F  K  F  W  L  M  W  K  A  K  G  T  V  G  F  E  N  Q  I
ATCTTCAAGTTCTGGCTGATGTGGAAAGCAAAGGGCACAGTGGGATTTGAAAACCAGATC 1440

 N  K  C  L  E  L  A  E  Y  L  Y  A  K  I  K  N  R  E  E  F
AACAAATGCCTGGAACTGGCTGAATACCTCTATGCCAAGATTAAAAACAGAGAAGAATTT 1500

 E  M  V  F  N  G  E  P  E  H  T  N  V  C  F  W  Y  I  P  Q
GAGATGGTTTTCAATGGCGAGCCTGAGCACACAAACGTCTGTTTTTGGTATATTCCACAA 1560

 S  L  R  G  V  P  D  S  P  Q  R  R  E  K  L  H  K  V  A  P
AGCCTCAGGGGTGTGCCAGACAGCCCTCAACGACGGGAAAAGCTACACAAGGTGGCTCCA 1620

 K  I  K  A  L  M  M  E  S  G  T  T  M  V  G  Y  Q  P  Q  G
AAAATCAAAGCCCTGATGATGGAGTCAGGTACGACCATGGTTGGCTACCAGCCCCAAGGG 1680

 D  K  A  N  F  F  R  M  V  I  S  N  P  A  A  T  Q  S  D  I
GACAAGGCCAACTTCTTCCGGATGGTCATCTCCAACCCAGCCGCTACCCAGTCTGACATT 1740

 D  F  L  I  E  E  I  E  R  L  G  Q  D  L  *
GACTTCCTCATTGAGGAGATAGAAAGACTGGGCCAGGATCTGTAA                1785
```

FIG. 7B

```
 M  A  S  S  T  P  S  S  S  A  T  S  S  N  A  G  A  D  P  N
ATGGCGTCTTCGACCCCATCTTCGTCCGCAACCTCCTCGAACGCGGGAGCGGACCCCAAT   60

 T  T  N  L  R  P  T  T  Y  D  T  W  C  G  V  A  H  G  C  T
ACCACTAACCTGCGCCCCACAACGTACGATACCTGGTGCGGCGTGGCCCATGGATGCACC  120

 R  K  L  G  L  K  I  C  G  F  L  Q  R  T  N  S  L  E  E  K
AGAAAACTGGGGCTCAAGATCTGCGGCTTCTTGCAAAGGACCAACAGCCTGGAAGAGAAG  180

 S  R  L  V  S  A  F  K  E  R  Q  S  S  K  N  L  L  S  C  E
AGTCGCCTTGTGAGTGCCTTCAAGGAGAGGCAATCCTCCAAGAACCTGCTTTCCTGTGAA  240

 N  S  D  R  D  A  R  F  R  R  T  E  T  D  F  S  N  L  F  A
AACAGCGACCGGGATGCCCGCTTCCGGCGCACAGAGACTGACTTCTCTAATCTGTTTGCT  300

 R  D  L  L  P  A  K  N  G  E  E  Q  T  V  Q  F  L  L  E  V
AGAGATCTGCTTCCGGCTAAGAACGGTGAGGAGCAAACCGTGCAATTCCTCCTGGAAGTG  360

 V  D  I  L  L  N  Y  V  R  K  T  F  D  R  S  T  K  V  L  D
GTGGACATACTCCTCAACTATGTCCGCAAGACATTTGATCGCTCCACCAAGGTGCTGGAC  420

 F  H  H  P  H  Q  L  L  E  G  M  E  G  F  N  L  E  L  S  D
TTTCATCACCCACACCAGTTGCTGGAAGGCATGGAGGGCTTCAACTTGGAGCTCTCTGAC  480

 H  P  E  S  L  E  Q  I  L  V  D  C  R  D  T  L  K  Y  G  V
CACCCCGAGTCCCTGGAGCAGATCCTGGTCGACTGCAGAGACACCTTGAAGTATGGGGTT  540

 R  T  G  H  P  R  F  F  N  Q  L  S  T  G  L  D  I  I  G  L
CGCACAGGTCATCCTCGATTTTTCAACCAGCTCTCCACTGGATTGGATATTATTGGCCTA  600

 A  G  E  W  L  T  S  T  A  N  T  N  M  F  T  Y  E  I  A  P
GCTGGAGAATGGCTGACATCAACGGCCAATACCAACATGTTCACATATGAAATTGCACCA  660

 V  F  V  L  M  E  Q  I  T  L  K  K  M  R  E  I  V  G  W  S
GTGTTTGTCCTCATGGAACAAATAACACTTAAGAAGATGAGAGAGATAGTTGGATGGTCA  720

 S  K  D  G  D  G  I  F  S  P
AGTAAAGATGGTGATGGGATATTTTCTCCT                                750
```

FIG.8

```
 T  A  N  T  N  M  F  T  Y  E  I  A  P  V  F  V  L  M  E  Q
ACGGCCAATACCAACATGTTCACATATGAAATTGCACCAGTGTTTGTCCTCATGGAACAA   681

 I  T  L  K  K  M  R  E  I  V  G  W  S  S  K  D  G  D  G  I
ATAACACTTAAGAAGATGAGAGAGATAGTTGGATGGTCAAGTAAAGATGGTGATGGGATA   741

 F  S  P  G  G  A  I  S  N  M  Y  S  I  M  A  A  R  Y  K  Y
TTTTCTCCTGGGGGCGCCATATCCAACATGTACAGCATCATGGCTGCTCGCTACAAGTAC   801

 F  P  E  V  K  T  K  G  M  A  A  V  P  K  L  V  L  F  T  S
TTCCCGGAAGTTAAGACAAAGGGCATGGCGGCTGTGCCTAAACTGGTCCTCTTCACCTCA   861

 E  Q  S  H  Y  S  I  K  K  A  G  A  A  L  G  F  G  T  D  N
GAACAGAGTCACTATTCCATAAAGAAAGCTGGGGCTGCACTTGGCTTTGGAACTGACAAT   921

 V  I  L  I  K  C  N  E  R  G  K  I  I  P  A  D  F  E  A  K
GTGATTTTGATAAAGTGCAATGAAAGGGGAAAATAATTCCAGCTGATTTTGAGGCAAAA   981

 I  L  E  A  K  Q  K  G  Y  V  P  F  Y  V  N  A  T  A  G  T
ATTCTTGAAGCCAAACAGAAGGGATATGTTCCCTTTTATGTCAATGCAACTGCTGGCACG  1041

 T  V  Y  G  A  F  D  P  I  Q  E  I  A  D  I  C  E  K  Y  N
ACTGTTTATGGAGCTTTTGATCCGATACAAGAGATTGCAGATATATGTGAGAAATATAAC  1101

 L  W  L  H  V  D  A  A  W  G  G  G  L  L  M  S  R  K  H  R
CTTTGGTTGCATGTCGATGCTGCCTGGGGAGGTGGGCTGCTCATGTCCAGGAAGCACCGC  1161

 H  K  L  N  G  I  E  R  A  N  S  V  T  W  N  P  H
CATAAACTCAACGGCATAGAAAGGGCCAACTCAGTCACCTGGAACCCTCAC           1212
```

FIG. 9

```
 G  I  E  R  A  N  S  V  T  N  N  P  H  K  M  M  G  V  L  L
GGCATAGAAAGGGCCAACTCAGTCACCTGGAACCCTCACAAGATGATGGGCGTGCTGTTG 1233

 Q  C  S  A  I  L  V  K  E  K  G  I  L  Q  G  C  N  Q  M  C
CAGTGCTCTGCCATTCTCGTCAAGGAAAAGGGTATACTCCAAGGATGCAACCAGATGTGT 1293

 A  G  Y  L  F  Q  P  D  K  Q  Y  D  V  S  Y  D  T  G  D  K
GCAGGATACCTCTTCCAGCCAGACAAGCAGTATGATGTCTCCTACGACACCGGGGACAAG 1353

 A  I  Q  C  G  R  H  V  D  I  F  K  F  W  L  M  W  K  A  K
GCAATTCAGTGTGGCCGCCACGTGGATATCTTCAAGTTCTGGCTGATGTGGAAAGCAAAG 1413

 G  T  V  G  F  E  N  Q  I  N  K  C  L  E  L  A  E  Y  L  Y
GGCACAGTGGGATTTGAAAACCAGATCAACAAATGCCTGGAACTGGCTGAATACCTCTAT 1473

 A  K  I  K  N  R  E  E  F  E  M  V  F  N  G  E  P  E  N  T
GCCAAGATTAAAAACAGAGAAGAATTTGAGATGGTTTTCAATGGCGAGCCTGAGCACACA 1533

 N  V  C  F  W  Y  I  P  Q  S  L  R  G  V  P  D  S  P  Q  R
AACGTCTGTTTTTGGTATATTCCACAAAGCCTCAGGGGTGTGCCAGACAGCCCTCAACGA 1593

 R  E  K  L  H  K  V  A  P  K  I  K  A  L  M  M  E  S  G  T
CGGGAAAAGCTACACAAGGTGGCTCCAAAAATCAAAGCCCTGATGATGGAGTCAGGTACG 1653

 T  M  V  G  Y  Q  P  Q  G  D  K  A  N  F  F  R  M  V  I  S
ACCATGGTTGGCTACCAGCCCCAAGGGGACAAGGCCAACTTCTTCCGGATGGTCATCTCC 1713

 N  P  A  A  T  Q  S  D  I  D  F  L  I  E  E  I  E  R  L  G
AACCCAGCCGCTACCCAGTCTGACATTGACTTCCTCATTGAGGAGATAGAAAGACTGGGC 1773

 Q  D  L  *
CAGGATCTGTAA                                                 1785
```

FIG. 10

```
 M  A  S  S  T  P  S  S  S  A  T  S  S  N  A  G  A  D  P  N
ATGGCGTCTTCGACCCCATCTTCGTCCGCAACCTCCTCGAACGCGGGAGCGGACCCCAAT    60

 T  T  N  L  R  P  T  T  Y  D  T  W  C  G  V  A  H  G  C  T
ACCACTAACCTGCGCCCCACAACGTACGATACCTGGTGCGGCGTGGCCCATGGATGCACC   120

 R  K  L  G  L  K  I  C  G  F  L  Q  R  T  N  S  L  E  E  K
AGAAAACTGGGGCTCAAGATCTGCGGCTTCTTGCAAAGGACCAACAGCCTGGAAGAGAAG   180

 S  R  L  V  S  A  F  K  E  R  Q  S  S  K  N  L  L  S  C  E
AGTCGCCTTGTGAGTGCCTTCAAGGAGAGGCAATCCTCCAAGAACCTGCTTTCCTGTGAA   240

 N  S  D  R  D  A  R  F  R  R  T  E  T  D  F  S  N  L  F  A
AACAGCGACCGGGATGCCCGCTTCCGGCGCACAGAGACTGACTTCTCTAATCTGTTTGCT   300

 R  D  L  L  P  A  K  N  G  E  E  Q  T  V  Q  F  L  L  E  V
AGAGATCTGCTTCCGGCTAAGAACGGTGAGGAGCAAACCGTGCAATTCCTCCTGGAAGTG   360

 V  D  I  L  L  N  Y  V  R  K  T  F  D  R  S  T  K  V  L  D
GTGGACATACTCCTCAACTATGTCCGCAAGACATTTGATCGCTCCACCAAGGTGCTGGAC   420

 F  H  H  P  H  Q  L  L  E  G  M  E  G  F  N  L  E  L  S  D
TTTCATCACCCACACCAGTTGCTGGAAGGCATGGAGGGCTTCAACTTGGAGCTCTCTGAC   480

 H  P  E  S  L  E  Q  I  L  V  D  C  R  D  T  L  K  Y  G  V
CACCCCGAGTCCCTGGAGCAGATCCTGGTCGACTGCAGAGACACCTTGAAGTATGGGGTT   540

 R  T  G  H  P  R  F  F  N  Q  L  S  T  G  L  D  I  I  G  L
CGCACAGGTCATCCTCGATTTTTCAACCAGCTCTCCACTGGATTGGATATTATTGGCCTA   600

 A  G  E  W  L  T  S  T  A  N  T  N  M  F  T  Y  E  I  A  P
GCTGGAGAATGGCTGACATCAACGGCCAATACCAACATGTTCACATATGAAATTGCACCA   660

 V  F  V  L  M  E  Q  I  T  L  K  K  M  R  E  I  V  G  W  S
GTGTTTGTCCTCATGGAACAAATAACACTTAAGAAGATGAGAGAGATAGTTGGATGGTCA   720

 S  K  D  G  D  G  I  F  S  P  G  G  A  I  S  N  M  Y  S  I
AGTAAAGATGGTGATGGATATTTTCTCCTGGGGGCGCCATATCCAACATGTACAGCATC   780

 M  A  A  R  Y  K  Y  F  P  E  V  K  T  K  G  M  A  A  V  P
ATGGCTGCTCGCTACAAGTACTTCCCGGAAGTTAAGACAAAGGGCATGGCGGCTGTGCCT   840

 K  L  V  L  F  T  S  E  Q  S  H  Y  S  I  K  K  A  G  A  A
AAACTGGTCCTCTTCACCTCAGAACAGAGTCACTATTCCATAAAGAAAGCTGGGGCTGCA   900

 L  G  F  G  T  D  N  V  I  L  I  K  C  N  E  R  G  K  I  I
CTTGGCTTTGGAACTGACAATGTGATTTTGATAAAGTGCAATGAAAGGGGGAAAATAATT   960

 P  A  D  F  E  A  K  I  L  E  A  K  Q  K  G  Y  V  P  F  Y
CCAGCTGATTTTGAGGCAAAAATTCTTGAAGCCAAACAGAAGGGATATGTTCCCTTTTAT  1020
```

FIG. 11A

```
 V  N  A  T  A  G  T  T  V  Y  G  A  F  D  P  I  Q  E  I  A
GTCAATGCAACTGCTGGCACGACTGTTTATGGAGCTTTTGATCCGATACAAGAGATTGCA 1080

 D  I  C  E  K  Y  N  L  W  L  H  V  D  A  A  W  G  G  G  L
GATATATGTGAGAAATATAACCTTTGGTTGCATGTCGATGCTGCCTGGGGAGGTGGGCTG 1140

 L  M  S  R  K  H  R  H  K  L  N  G  I  E  R  A  N  S  V  T
CTCATGTCCAGGAAGCACCGCCATAAACTCAACGGCATAGAAAGGGCCAACTCAGTCACC 1200

 N  N  P  H  K  M  M  G  V  L  L  Q  C  S  A  I  L  V  K  E
TGGAACCCTCACAAGATGATGGGCGTGCTGTTGCAGTGCTCTGCCATTCTCGTCAAGGAA 1260

 K  G  I  L  Q  G  C  N  Q  M  C  A  G  Y  L  F  Q  P  D  K
AAGGGTATACTCCAAGGATGCAACCAGATGTGTGCAGGATACCTCTTCCAGCCAGACAAG 1320

 Q  Y  D  V  S  Y  D  T  G  D  K  A  I  Q  C  G  R  M  V  D
CAGTATGATGTCTCCTACGACACCGGGGACAAGGCAATTCAGTGTGGCCGCCACGTGGAT 1380

 I  F  K  F  W  L  M  W  K  A  K  G  T  V  G  F  E  N  Q  I
ATCTTCAAGTTCTGGCTGATGTGGAAAGCAAAGGGCACAGTGGGATTTGAAAACCAGATC 1440

 N  K  C  L  E  L  A  E  Y  L  Y  A  K  I  K  N  R  E  E  F
AACAAATGCCTGGAACTGGCTGAATACCTCTATGCCAAGATTAAAAACAGAGAAGAATTT 1500

 E  M  V  F  N  G  E  P  E  H  T  N  V  C  F  W  Y  I  P  Q
GAGATGGTTTTCAATGGCGAGCCTGAGCACACAAACGTCTGTTTTTGGTATATTCCACAA 1560

 S  L  R  G  V  P  D  S  P  Q  R  R  E  K  L  H  K  V  A  P
AGCCTCAGGGGTGTGCCAGACAGCCCTCAACGACGGGAAAAGCTACACAAGGTGGCTCCA 1620

 K  I  K  A  L  M  M  E  S  G  T  T  M  V  G  Y  Q  P  Q  G
AAAATCAAAGCCCTGATGATGGAGTCAGGTACGACCATGGTTGGCTACCAGCCCCAAGGG 1680

 D  K  A  N  F  F  R  M  V  I  S  N  P  A  A  T  Q  S  D  I
GACAAGGCCAACTTCTTCCGGATGGTCATCTCCAACCCAGCCGCTACCCAGTCTGACATT 1740

 D  F  L  I  E  E  I  E  R  L  G  Q  D  L  *
GACTTCCTCATTGAGGAGATAGAAAGACTGGGCCAGGATCTGTAA                1785
```

FIG. 11B

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
( A ) LENGTH: 543 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:1:

```
ATTGCACCCG TGTTTGTTCT CATGGAACAG ATTACTCTTA AGAAGATGAG AAAGATCGTT    60
GGATGGTCAA ATAAAGATGG TGATGGGTTA TTTTCTCCTG GGGGAGCCAT ATCCAATATG   120
TACAGCACCA TGGCTGCTCG TTACAAGTAC TTCCCAGAAG TGAAGACAAA AGGCATGGCG   180
GCTGTGCCCA AACTGGTCCT CTTCACCTCA GAACACAGTC ACTATTCCAT AAAGAAAGCC   240
GGGGCTGCGC TTGGCTTTGG AACCGACAAT GTGATTTTGA TAAAGTGCAA TGAAAGGGGG   300
AAGATAATTC CGGCTGATTT AGAGGCAAAA ATTCTTGATG CCAAACAAAA GGGCTATGTT   360
CCCCTCTATG TCAATGCAAC CGCAGGCACG ACTGTTTACG GAGCATTCGA TCCAATCCAG   420
GAAATTGCGG ACATATGTGA GAAATACAAC CTTTGGCTGC ATGTGGATGC TGCCTGGGGT   480
GGTGGACTGC TCATGTCCCG GAAGCACCGC CACAAACTCA GCGGCATAGA AAGGGCCAAT   540
TCA                                                                 543
```

( 2 ) INFORMATION FOR SEQ ID NO:2:

( i ) SEQUENCE CHARACTERISTICS:
( A ) LENGTH: 543 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:2:

```
ATTGCACCCG TGTTTGTTCT CATGGAACAG ATTACTCTTA AGAAGATGAG AAAGATCGTT    60
GGATGGTCAA ATAAAGATGG TGATGGGTTA CTTTCTCCTG GGGGAGCCAT ATCCAATATG   120
TACAGCATCA TGGCTGCTCG TTACAAGTAC TTCCCAGAAG TGAAGACAAA AGGCATGGCG   180
```

```
GCTGTGCCCA AACTGGTCCT CTTCACCTCA GAACACAGTC ACTATTCCAT AAAGAAAGCC    240
GGGGCTGCGC TTGGCTTTGG AACCGACAAT GTGATTTTGA TAAAGTGCAA TGAAAGGGGG    300
AAGATAATTC CGGCTGATTT AGAGGCAAAA ATTCTTGATG CCAAACAAAA GGGCTATGTT    360
CCCCTTTATG TCAATGCAAC CGCAGGCACG ACTGTTTACG GAGCATTCGA TCCAATCCAG    420
GAAATTGCGG ACATATGTGA GAAATACAAC CTTTGGCTGC ATGTGGATGC TGCCTGGGGT    480
GGTGGACTGC TCATGTCCCG GAAGCACCGC CACAAACTCA GCGGCATAGA AAGGGCCAAT    540
TCA                                                                  543
```

( 2 ) INFORMATION FOR SEQ ID NO:3:

( i ) SEQUENCE CHARACTERISTICS:
( A ) LENGTH: 181 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:3:

```
Ile Ala Pro Val Phe Val Leu Met Glu Gln Ile Thr Leu Lys Lys Met
1               5                   10                  15

Arg Lys Ile Val Gly Trp Ser Asn Lys Asp Gly Asp Gly Leu Phe Ser
            20                  25                  30

Pro Gly Gly Ala Ile Ser Asn Met Tyr Ser Thr Met Ala Ala Arg Tyr
        35                  40                  45

Lys Tyr Phe Pro Glu Val Lys Thr Lys Gly Met Ala Ala Val Pro Lys
    50                  55                  60

Leu Val Leu Phe Thr Ser Glu His Ser His Tyr Ser Ile Lys Lys Ala
65                  70                  75                  80

Gly Ala Ala Leu Gly Phe Gly Thr Asp Asn Val Ile Leu Ile Lys Cys
                85                  90                  95

Asn Glu Arg Gly Lys Ile Ile Pro Ala Asp Leu Glu Ala Lys Ile Leu
            100                 105                 110

Asp Ala Lys Gln Lys Gly Tyr Val Pro Leu Tyr Val Asn Ala Thr Ala
        115                 120                 125

Gly Thr Thr Val Tyr Gly Ala Phe Asp Pro Ile Gln Glu Ile Ala Asp
    130                 135                 140

Ile Cys Glu Lys Tyr Asn Leu Trp Leu His Val Asp Ala Ala Trp Gly
145                 150                 155                 160

Gly Gly Leu Leu Met Ser Arg Lys His Arg His Lys Leu Ser Gly Ile
                165                 170                 175

Glu Arg Ala Asn Ser
            180
```

( 2 ) INFORMATION FOR SEQ ID NO:4:

( i ) SEQUENCE CHARACTERISTICS:
( A ) LENGTH: 181 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:4:

```
Ile Ala Pro Val Phe Val Leu Met Glu Gln Ile Thr Leu Lys Lys Met
1               5                   10                  15

Arg Lys Ile Val Gly Trp Ser Asn Lys Asp Gly Asp Gly Ile Leu Ser
```

20 25 30

Pro Gly Gly Ala Ile Ser Asn Met Tyr Ser Ile Met Ala Ala Arg Tyr
35 40 45

Lys Tyr Phe Pro Glu Val Lys Thr Lys Gly Met Ala Ala Val Pro Lys
50 55 60

Leu Val Leu Phe Thr Ser Glu His Ser His Tyr Ser Ile Lys Lys Ala
65 70 75 80

Gly Ala Ala Leu Gly Phe Gly Thr Asp Asn Val Ile Leu Ile Lys Cys
85 90 95

Asn Glu Arg Gly Lys Ile Ile Pro Ala Asp Leu Glu Ala Lys Ile Leu
100 105 110

Asp Ala Lys Gln Lys Gly Tyr Val Pro Leu Tyr Val Asn Ala Thr Ala
115 120 125

Gly Thr Thr Val Tyr Gly Ala Phe Asp Pro Ile Gln Glu Ile Ala Asp
130 135 140

Ile Cys Glu Lys Tyr Asn Leu Trp Leu His Val Asp Ala Ala Trp Gly
145 150 155 160

Gly Gly Leu Leu Met Ser Arg Lys His Arg His Lys Leu Ser Gly Ile
165 170 175

Glu Arg Ala Asn Ser
180

( 2 ) INFORMATION FOR SEQ ID NO:5:

( i ) SEQUENCE CHARACTERISTICS:
( A ) LENGTH: 181 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:5:

Ile Ala Pro Val Phe Val Leu Met Glu Gln Ile Thr Leu Lys Lys Met
1 5 10 15

Arg Glu Ile Val Gly Trp Ser Ser Lys Asp Gly Asp Gly Ile Phe Ser
20 25 30

Pro Gly Gly Ala Ile Ser Asn Met Tyr Ser Ile Met Ala Ala Arg Tyr
35 40 45

Lys Phe Phe Pro Glu Val Lys Thr Lys Gly Met Ala Ala Val Pro Lys
50 55 60

Leu Val Leu Phe Thr Ser Glu His Ser His Tyr Ser Ile Lys Lys Ala
65 70 75 80

Gly Ala Ala Leu Gly Phe Gly Thr Asp Asn Val Ile Leu Ile Lys Cys
85 90 95

Asn Glu Arg Gly Lys Ile Ile Pro Ala Asp Leu Glu Ala Lys Ile Leu
100 105 110

Glu Ala Lys Gln Lys Gly Tyr Val Pro Leu Tyr Val Asn Ala Thr Ala
115 120 125

Gly Thr Thr Val Tyr Gly Ala Phe Asp Pro Ile Gln Glu Ile Ala Asp
130 135 140

Ile Cys Glu Lys Tyr Asn Leu Trp Leu His Val Asp Ala Ala Trp Gly
145 150 155 160

Gly Gly Leu Leu Met Ser Arg Lys His Arg His Lys Leu Ser Gly Ile
165 170 175

Glu Arg Ala Asn Ser
180

( 2 ) INFORMATION FOR SEQ ID NO:6:

( i ) SEQUENCE CHARACTERISTICS:
( A ) LENGTH: 1782 base pairs
( B ) TYPE: nucleic acid
( C ) STRANDEDNESS: single
( D ) TOPOLOGY: linear ( i i ) MOLECULE TYPE: cDNA to mRNA ( x i ) SEQUENCE DESCRIPTION: SEQ ID NO:6:

```
ATGGCGTCTT CCACTCCTTC GCCTGCAACC TCCTCGAACG CGGGAGCGGA TCCTAATACT   60
ACCAACCTGC GCCCTACAAC GTATGATACT TGGTGTGGCG TAGCCCATGG ATGCACCAGA  120
AAACTGGGCC TGAAGATCTG TGGCTTCTTA CAAAGGACCA ATAGCCTGGA AGAGAAGAGT  180
CGTCTTGTGA GCGCCTTCAG GGAGAGGCAG TCCTCCAAGA ACCTGCTTTC CTGTGAAAAC  240
AGTGACCAGG GTGCCCGCTT CCGGCGCACA GAGACCGACT TCTCCAACCT GTTTGCTCAA  300
GATCTGCTTC CAGCTAAGAA CGGGGAGGAG CAAACTGCGC AGTTCTTGCT GGAAGTGGTA  360
GACATACTCC TCAACTATGT CCGCAAGACA TTTGATCGCT CCACCAAGGT TCTGGATTTC  420
CACCACCCAC ACCAGTTGCT GGAAGGCATG GAAGGCTTTA ATTTGGAGCT GTCTGACCAC  480
CCCGAGTCTC TGGAGCAGAT CCTGGTTGAC TGTAGAGACA CCCTGAAGTA CGGGGTTCGC  540
ACAGGTCACC CTCGATTTTT CAACCAGCTC TCTACTGGTT TGGATATCAT TGGTTTAGCT  600
GGCGAATGGC TGACATCGAC TGCCAATACC AATATGTTCA CATATGAAAT TGCACCCGTG  660
TTTGTTCTCA TGGAACAGAT TACTCTTAAG AAGATGAGAA AGATCGTTGG ATGGTCAAAT  720
AAAGATGGTG ATGGGATATT TTCTCCTGGG GGAGCCATAT CCAATATGTA CAGCATCATG  780
GCTGCTCGTT ACAAGTACTT CCCAGAAGTG AAGACAAAAG GCATGGCGGC TGTGCCCAAA  840
CTGGTCCTCT TCACCTCAGA ACACAGTCAC TATTCCATAA AGAAAGCCGG GGCTGCGCTT  900
GGCTTTGGAA CCGACAATGT GATTTTGATA AAGTGCAATG AAAGGGGGAA GATAATTCCG  960
GCTGATTTAG AGGCAAAAAT TCTTGATGCC AAACAAAAGG GCTATGTTCC CCTTTATGTC 1020
AATGCAACCG CAGGCACGAC TGTTTACGGA GCATTCGATC CAATCCAGGA AATTGCGGAC 1080
ATATGTGAGA AATACAACCT TTGGCTGCAT GTGGATGCTG CCTGGGGTGG TGGACTGCTC 1140
ATGTCCCGGA AGCACCGCCA CAAACTCAGC GGCATAGAAA GGGCCAATTC AGTCACCTGG 1200
AACCCTCACA AGATGATGGG CGTGCTGCTC CAGTGCTCTG CCATTCTGGT CAAGGAAAAG 1260
GGTATACTCC AAGGATGCAA CCAGATGTGT GCAGGCTACC TCTTCCAGCC AGACAAGCAG 1320
TATGACGTCT CCTATGACAC CGGGGACAAG GCGATTCAGT GTGGCCGCCA TGTGGACATC 1380
TTCAAGTTCT GGCTGATGTG GAAAGCAAAG GGCACCGTGG GATTTGAAAA CCAGATCAAC 1440
AAATGCCTGG AGCTGGCTGA TTACCTCTAC GCCAAGATTA AAAACAGAGA AGAGTTTGAG 1500
ATGGTTTTCG ATGGTGAGCC TGAGCACACA AATGTCTGTT TCTGGTACAT TCCACAAAGC 1560
CTTCGAGGGG TTCCAGATAG CCCTGAGCGA CGAGAAAAGC TACACAGGGT GGCTCCCAAG 1620
ATCAAAGCTC TGATGATGGA GTCAGGAACA ACCATGGTGG GCTACCAGCC TCAAGGGGAC 1680
AAGGCCAACT TCTTCCGGAT GGTCATCTCT AACCCAGCCG CCACCCAGTC TGACATCGAT 1740
TTCCTCATTG AGGAGATAGA GAGGTTGGGC CAGGATCTGT AA                   1782
```

( 2 ) INFORMATION FOR SEQ ID NO:7:

( i ) SEQUENCE CHARACTERISTICS:
( A ) LENGTH: 609 base pairs
( B ) TYPE: nucleic acid ( C ) STRANDEDNESS: single
( D ) TOPOLOGY: linear ( i i ) MOLECULE TYPE: cDNA to mRNA ( x i ) SEQUENCE DESCRIPTION: SEQ ID NO:7:

```
ATGGCGTCTT CCACTCCTTC GCCTGCAACC TCCTCGAACG CGGGAGCGGA TCCTAATACT    60
ACCAACCTGC GCCCTACAAC GTATGATACT TGGTGTGGCG TAGCCCATGG ATGCACCAGA   120
AAACTGGGCC TGAAGATCTG TGGCTTCTTA CAAAGGACCA ATAGCCTGGA AGAGAAGAGT   180
CGTCTTGTGA GCGCCTTCAG GGAGAGGCAG TCCTCCAAGA ACCTGCTTTC CTGTGAAAAC   240
AGTGACCAGG GTGCCCGCTT CCGGCGCACA GAGACCGACT TCTCCAACCT GTTTGCTCAA   300
GATCTGCTTC CAGCTAAGAA CGGGGAGGAG CAAACTGCGC AGTTCTTGCT GGAAGTGGTA   360
GACATACTCC TCAACTATGT CCGCAAGACA TTTGATCGCT CCACCAAGGT TCTGGATTTC   420
CACCACCCAC ACCAGTTGCT GGAAGGCATG GAAGGCTTTA ATTTGGAGCT GTCTGACCAC   480
CCCGAGTCTC TGGAGCAGAT CCTGGTTGAC TGTAGAGACA CCCTGAAGTA CGGGGTTCGC   540
ACAGGTCACC CTCGATTTTT CAACCAGCTC TCTACTGGTT TGGATATCAT TGGTTTAGCT   600
GGCGAATGG                                                           609
```

( 2 ) INFORMATION FOR SEQ ID NO:8:

( i ) SEQUENCE CHARACTERISTICS:
( A ) LENGTH: 618 base pairs
( B ) TYPE: nucleic acid
( C ) STRANDEDNESS: single
( D ) TOPOLOGY: linear ( i i ) MOLECULE TYPE: cDNA to mRNA ( x i ) SEQUENCE DESCRIPTION: SEQ ID NO:8:

```
GGTTTAGCTG GCGAATGGCT GACATCGACT GCCAATACCA ATATGTTCAC ATATGAAATT    60
GCACCCGTGT TTGTTCTCAT GGAACAGATT ACTCTTAAGA AGATGAGAAA GATCGTTGGA   120
TGGTCAAATA AAGATGGTGA TGGGATATTT TCTCCTGGGG GAGCCATATC CAATATGTAC   180
AGCATCATGG CTGCTCGTTA CAAGTACTTC CCAGAAGTGA AGACAAAAGG CATGGCGGCT   240
GTGCCCAAAC TGGTCCTCTT CACCTCAGAA CACAGTCACT ATTCCATAAA GAAAGCCGGG   300
GCTGCGCTTG GCTTTGGAAC CGACAATGTG ATTTTGATAA AGTGCAATGA AAGGGGGAAG   360
ATAATTCCGG CTGATTTAGA GGCAAAAATT CTTGATGCCA AACAAAAGGG CTATGTTCCC   420
CTTTATGTCA ATGCAACCGC AGGCACGACT GTTTACGGAG CATTCGATCC AATCCAGGAA   480
ATTGCGGACA TATGTGAGAA ATACAACCTT TGGCTGCATG TGGATGCTGC CTGGGGTGGT   540
GGACTGCTCA TGTCCCGGAA GCACCGCCAC AAACTCAGCG GCATAGAAAG GGCCAATTCA   600
GTCACCTGGA ACCCTCAC                                                 618
```

( 2 ) INFORMATION FOR SEQ ID NO:9:

( i ) SEQUENCE CHARACTERISTICS:
( A ) LENGTH: 612 base pairs
( B ) TYPE: nucleic acid
( C ) STRANDEDNESS: single
( D ) TOPOLOGY: linear ( i i ) MOLECULE TYPE: cDNA to mRNA ( x i ) SEQUENCE DESCRIPTION: SEQ ID NO:9:

```
GGCATAGAAA GGGCCAATTC AGTCACCTGG AACCCTCACA AGATGATGGG CGTGCTGCTC    60
CAGTGCTCTG CCATTCTGGT CAAGGAAAAG GGTATACTCC AAGGATGCAA CCAGATGTGT   120
```

```
GCAGGCTACC TCTTCCAGCC AGACAAGCAG TATGACGTCT CCTATGACAC CGGGGACAAG  180
GCGATTCAGT GTGGCCGCCA TGTGGACATC TTCAAGTTCT GGCTGATGTG GAAAGCAAAG  240
GGCACCGTGG GATTTGAAAA CCAGATCAAC AAATGCCTGG AGCTGGCTGA TTACCTCTAC  300
GCCAAGATTA AAAACAGAGA AGAGTTTGAG ATGGTTTTCG ATGGTGAGCC TGAGCACACA  360
AATGTCTGTT TCTGGTACAT TCCACAAAGC CTTAGAGGGG TTCCAGATAG CCCTGAGCGA  420
CGAGAAAAGC TACACAGGGT GGCTCCCAAG ATCAAAGCTC TGATGATGGA GTCAGGAACA  480
ACCATGGTCG GCTACCAGCC TCAAGGGGAC AAGGCCAACT TCTTCCGGAT GGTCATCTCT  540
AACCCAGCCG CCACCCAGTC TGACATCGAT TTCCTCATTG AGGAGATAGA GAGGTTGGGC  600
CAGGATCTGT AA                                                      612
```

( 2 ) INFORMATION FOR SEQ ID NO:10:

( i ) SEQUENCE CHARACTERISTICS:
( A ) LENGTH: 1785 base pairs
( B ) TYPE: nucleic acid
( C ) STRANDEDNESS: single
( D ) TOPOLOGY: linear ( i i ) MOLECULE TYPE: cDNA to mRNA ( x i ) SEQUENCE DESCRIPTION: SEQ ID NO:10:

```
ATGGCGTCTT CGACCCCATC TTCGTCCGCA ACCTCCTCGA ACGCGGGAGC GGACCCCAAT    60
ACCACTAACC TGCGCCCCAC AACGTACGAT ACCTGGTGCG GCGTGGCCCA TGGATGCACC   120
AGAAAACTGG GGCTCAAGAT CTGCGGCTTC TTGCAAAGGA CCAACAGCCT GGAAGAGAAG   180
AGTCGCCTTG TGAGTGCCTT CAAGGAGAGG CAATCCTCCA AGAACCTGCT TTCCTGTGAA   240
AACAGCGACC GGGATGCCCG CTTCCGGCGC ACAGAGACTG ACTTCTCTAA TCTGTTTGCT   300
AGAGATCTGC TTCCGGCTAA GAACGGTGAG GAGCAAACCG TGCAATTCCT CCTGGAAGTG   360
GTGGACATAC TCCTCAACTA TGTCCGCAAG ACATTTGATC GCTCCACCAA GGTGCTGGAC   420
TTTCATCACC CACACCAGTT GCTGGAAGGC ATGGAGGGCT TCAACTTGGA GCTCTCTGAC   480
CACCCCGAGT CCCTGGAGCA GATCCTGGTC GACTGCAGAG ACACCTTGAA GTATGGGGTT   540
CGCACAGGTC ATCCTCGATT TTTCAACCAG CTCTCCACTG GATTGGATAT TATTGGCCTA   600
GCTGGAGAAT GGCTGACATC AACGGCCAAT ACCAACATGT TCACATATGA AATTGCACCA   660
GTGTTTGTCC TCATGGAACA AATAACACTT AAGAAGATGA GAGAGATAGT TGGATGGTCA   720
AGTAAAGATG GTGATGGGAT ATTTTCTCCT GGGGGCGCCA TATCCAACAT GTACAGCATC   780
ATGGCTGCTC GCTACAAGTA CTTCCCGGAA GTTAAGACAA AGGGCATGGC GGCTGTGCCT   840
AAACTGGTCC TCTTCACCTC AGAACAGAGT CACTATTCCA TAAAGAAAGC TGGGGCTGCA   900
CTTGGCTTTG GAACTGACAA TGTGATTTTG ATAAAGTGCA ATGAAAGGGG GAAAATAATT   960
CCAGCTGATT TTGAGGCAAA AATTCTTGAA GCCAAACAGA AGGGATATGT TCCCTTTTAT  1020
GTCAATGCAA CTGCTGGCAC GACTGTTTAT GGAGCTTTTG ATCCGATACA AGAGATTGCA  1080
GATATATGTG AGAAATATAA CCTTTGGTTG CATGTCGATG CTGCCTGGGG AGGTGGGCTG  1140
CTCATGTCCA GGAAGCACCG CCATAAACTC AACGGCATAG AAAGGGCCAA CTCAGTCACC  1200
TGGAACCCTC ACAAGATGAT GGGCGTGCTG TTGCAGTGCT CTGCCATTCT CGTCAAGGAA  1260
AAGGGTATAC TCCAAGGATG CAACCAGATG TGTGCAGGAT ACCTCCTCCA GCCAGACAAG  1320
CAGTATGATG TCTCCTACGA CACCGGGGAC AAGGCAATTC AGTGTGGCCG CCACGTGGAT  1380
ATCTTCAAGT TCTGGCTGAT GTGGAAAGCA AAGGGCACAG TGGGATTTGA AAACCAGATC  1440
```

-continued

```
AACAAATGCC TGGAACTGGC TGAATACCTC TATGCCAAGA TTAAAAACAG AGAAGAATTT 1500
GAGATGGTTT TCAATGGCGA GCCTGAGCAC ACAAACGTCT GTTTTTGGTA TATTCCACAA 1560
AGCCTCAGGG GTGTGCCAGA CAGCCCTCAA CGACGGGAAA AGCTACACAA GGTGGCTCCA 1620
AAAATCAAAG CCCTGATGAT GGAGTCAGGT ACGACCATGG TTGGCTACCA GCCCCAAGGG 1680
GACAAGGCCA ACTTCTTCCG GATGGTCATC TCCAACCCAG CCGCTACCCA GTCTGACATT 1740
GACTTCCTCA TTGAGGAGAT AGAAAGACTG GGCCAGGATC TGTAA                 1785
```

( 2 ) INFORMATION FOR SEQ ID NO:11:

( i ) SEQUENCE CHARACTERISTICS:
( A ) LENGTH: 750 base pairs
( B ) TYPE: nucleic acid
( C ) STRANDEDNESS: single
( D ) TOPOLOGY: linear ( i i ) MOLECULE TYPE: cDNA to mRNA ( x i ) SEQUENCE DESCRIPTION: SEQ ID NO:11:

```
ATGGCGTCTT CGACCCCATC TTCGTCCGCA ACCTCCTCGA ACGCGGGAGC GGACCCCAAT   60
ACCACTAACC TGCGCCCCAC AACGTACGAT ACCTGGTGCG GCGTGGCCCA TGGATGCACC  120
AGAAAACTGG GGCTCAAGAT CTGCGGCTTC TTGCAAAGGA CCAACAGCCT GGAAGAGAAG  180
AGTCGCCTTG TGAGTGCCTT CAAGGAGAGG CAATCCTCCA AGAACCTGCT TTCCTGTGAA  240
AACAGCGACC GGGATGCCCG CTTCCGGCGC ACAGAGACTG ACTTCTCTAA TCTGTTTGCT  300
AGAGATCTGC TTCCGGCTAA GAACGGTGAG GAGCAAACCG TGCAATTCCT CCTGGAAGTG  360
GTGGACATAC TCCTCAACTA TGTCCGCAAG ACATTTGATC GCTCCACCAA GGTGCTGGAC  420
TTTCATCACC CACACCAGTT GCTGGAAGGC ATGGAGGGCT TCAACTTGGA GCTCTCTGAC  480
CACCCCGAGT CCCTGGAGCA GATCCTGGTC GACTGCAGAG ACACCTTGAA GTATGGGGTT  540
CGCACAGGTC ATCCTCGATT TTTCAACCAG CTCTCCACTG GATTGGATAT TATTGGCCTA  600
GCTGGAGAAT GGCTGACATC AACGGCCAAT ACCAACATGT TCACATATGA AATTGCACCA  660
GTGTTTGTCC TCATGGAACA AATAACACTT AAGAAGATGA GAGAGATAGT TGGATGGTCA  720
AGTAAAGATG GTGATGGGAT ATTTTCTCCT                                   750
```

( 2 ) INFORMATION FOR SEQ ID NO:12:

( i ) SEQUENCE CHARACTERISTICS:
( A ) LENGTH: 591 base pairs
( B ) TYPE: nucleic acid
( C ) STRANDEDNESS: single
( D ) TOPOLOGY: linear ( i i ) MOLECULE TYPE: cDNA to mRNA ( x i ) SEQUENCE DESCRIPTION: SEQ ID NO:12:

```
ACGGCCAATA CCAACATGTT CACATATGAA ATTGCACCAG TGTTTGTCCT CATGGAACAA   60
ATAACACTTA AGAAGATGAG AGAGATAGTT GGATGGTCAA GTAAAGATGG TGATGGGATA  120
TTTTCTCCTG GGGGCGCCAT ATCCAACATG TACAGCATCA TGGCTGCTCG CTACAAGTAC  180
TTCCCGGAAG TTAAGACAAA GGGCATGGCG GCTGTGCCTA AACTGGTCCT CTTCACCTCA  240
GAACAGAGTC ACTATTCCAT AAAGAAAGCT GGGGCTGCAC TTGGCTTTGG AACTGACAAT  300
GTGATTTTGA TAAAGTGCAA TGAAAGGGGG AAAATAATTC CAGCTGATTT TGAGGCAAAA  360
ATTCTTGAAG CCAAACAGAA GGGATATGTT CCCTTTTATG TCAATGCAAC TGCTGGCACG  420
ACTGTTTATG GAGCTTTTGA TCCGATACAA GAGATTGCAG ATATATGTGA GAAATATAAC  480
```

-continued

```
CTTTGGTTGC ATGTCGATGC TGCCTGGGGA GGTGGGCTGC TCATGTCCAG GAAGCACCGC     540
CATAAACTCA ACGGCATAGA AAGGGCCAAC TCAGTCACCT GGAACCCTCA C              591
```

( 2 ) INFORMATION FOR SEQ ID NO:13:

( i ) SEQUENCE CHARACTERISTICS:
( A ) LENGTH: 612 base pairs
( B ) TYPE: nucleic acid
( C ) STRANDEDNESS: single
( D ) TOPOLOGY: linear ( i i ) MOLECULE TYPE: cDNA to mRNA ( x i ) SEQUENCE DESCRIPTION: SEQ ID NO:13:

```
GGCATAGAAA GGGCCAACTC AGTCACCTGG AACCCTCACA AGATGATGGG CGTGCTGTTG      60
CAGTGCTCTG CCATTCTCGT CAAGGAAAAG GGTATACTCC AAGGATGCAA CCAGATGTGT     120
GCAGGATACC TCTTCCAGCC AGACAAGCAG TATGATGTCT CCTACGACAC CGGGGACAAG     180
GCAATTCAGT GTGGCCGCCA CGTGGATATC TTCAAGTTCT GGCTGATGTG GAAAGCAAAG     240
GGCACAGTGG GATTTGAAAA CCAGATCAAC AAATGCCTGG AACTGGCTGA ATACCTCTAT     300
GCCAAGATTA AAAACAGAGA AGAATTTGAG ATGGTTTTCA ATGGCGAGCC TGAGCACACA     360
AACGTCTGTT TTTGGTATAT TCCACAAAGC CTCAGGGGTG TGCCAGACAG CCCTCAACGA     420
CGGGAAAAGC TACACAAGGT GGCTCCAAAA ATCAAAGCCC TGATGATGGA GTCAGGTACG     480
ACCATGGTTG GCTACCAGCC CCAAGGGGAC AAGGCCAACT TCTTCCGGAT GGTCATCTCC     540
AACCCAGCCG CTACCCAGTC TGACATTGAC TTCCTCATTG AGGAGATAGA AAGACTGGGC     600
CAGGATCTGT AA                                                         612
```

( 2 ) INFORMATION FOR SEQ ID NO:14:

( i ) SEQUENCE CHARACTERISTICS:
( A ) LENGTH: 1785 base pairs
( B ) TYPE: nucleic acid
( C ) STRANDEDNESS: single
( D ) TOPOLOGY: linear ( i i ) MOLECULE TYPE: cDNA to mRNA ( x i ) SEQUENCE DESCRIPTION: SEQ ID NO:14:

```
ATGGCGTCTT CGACCCCATC TTCGTCCGCA ACCTCCTCGA ACGCGGGAGC GGACCCCAAT      60
ACCACTAACC TGCGCCCCAC AACGTACGAT ACCTGGTGCG GCGTGGCCCA TGGATGCACC     120
AGAAAACTGG GGCTCAAGAT CTGCGGCTTC TTGCAAAGGA CCAACAGCCT GGAAGAGAAG     180
AGTCGCCTTG TGAGTGCCTT CAAGGAGAGG CAATCCTCCA AGAACCTGCT TTCCTGTGAA     240
AACAGCGACC GGGATGCCCG CTTCCGGCGC ACAGAGACTG ACTTCTCTAA TCTGTTTGCT     300
AGAGATCTGC TTCCGGCTAA GAACGGTGAG GAGCAAACCG TGCAATTCCT CCTGGAAGTG     360
GTGGACATAC TCCTCAACTA TGTCCGCAAG ACATTTGATC GCTCCACCAA GGTGCTGGAC     420
TTTCATCACC CACACCAGTT GCTGGAAGGC ATGGAGGGCT TCAACTTGGA GCTCTCTGAC     480
CACCCCGAGT CCCTGGAGCA GATCCTGGTC GACTGCAGAG ACACCTTGAA GTATGGGGTT     540
CGCACAGGTC ATCCTCGATT TTTCAACCAG CTCTCCACTG GATTGGATAT TATTGGCCTA     600
GCTGGAGAAT GGCTGACATC AACGGCCAAT ACCAACATGT TCACATATGA AATTGCACCA     660
GTGTTTGTCC TCATGGAACA AATAACACTT AAGAAGATGA GAGAGATAGT TGGATGGTCA     720
AGTAAAGATG GTGATGGGAT ATTTTCTCCT GGGGGCGCCA TATCCAACAT GTACAGCATC     780
ATGGCTGCTC GCTACAAGTA CTTCCCGGAA GTTAAGACAA AGGGCATGGC GGCTGTGCCT     840
```

-continued

```
AAACTGGTCC TCTTCACCTC AGAACAGAGT CACTATTCCA TAAAGAAAGC TGGGGCTGCA  900
CTTGGCTTTG GAACTGACAA TGTGATTTTG ATAAAGTGCA ATGAAAGGGG GAAAATAATT  960
CCAGCTGATT TTGAGGCAAA AATTCTTGAA GCCAAACAGA AGGGATATGT TCCCTTTTAT 1020
GTCAATGCAA CTGCTGGCAC GACTGTTTAT GGAGCTTTTG ATCCGATACA AGAGATTGCA 1080
GATATATGTG AGAAATATAA CCTTTGGTTG CATGTCGATG CTGCCTGGGG AGGTGGGCTG 1140
CTCATGTCCA GGAAGCACCG CCATAAACTC AACGGCATAG AAAGGGCCAA CTCAGTCACC 1200
TGGAACCCTC ACAAGATGAT GGGCGTGCTG TTGCAGTGCT CTGCCATTCT CGTCAAGGAA 1260
AAGGGTATAC TCCAAGGATG CAACCAGATG TGTGCAGGAT ACCTCTTCCA GCCAGACAAG 1320
CAGTATGATG TCTCCTACGA CACCGGGGAC AAGGCAATTC AGTGTGGCCG CCACGTGGAT 1380
ATCTTCAAGT TCTGGCTGAT GTGGAAAGCA AAGGGCACAG TGGGATTTGA AAACCAGATC 1440
AACAAATGCC TGGAACTGGC TGAATACCTC TATGCCAAGA TTAAAAACAG AGAAGAATTT 1500
GAGATGGTTT TCAATGGCGA GCCTGAGCAC ACAAACGTCT GTTTTTGGTA TATTCCACAA 1560
AGCCTCAGGG GTGTGCCAGA CAGCCCTCAA CGACGGGAAA AGCTACACAA GGTGGCTCCA 1620
AAAATCAAAG CCCTGATGAT GGAGTCAGGT ACGACCATGG TTGGCTACCA GCCCCAAGGG 1680
GACAAGGCCA ACTTCTTCCG GATGGTCATC TCCAACCCAG CCGCTACCCA GTCTGACATT 1740
GACTTCCTCA TTGAGGAGAT AGAAAGACTG GGCCAGGATC TGTAA                1785
```

( 2 ) INFORMATION FOR SEQ ID NO:15:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:15:

```
ATTGGATCCA CCGAGCTGAT GGCGTCTTC  29
```

( 2 ) INFORMATION FOR SEQ ID NO:16:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:16:

```
CCGAATTCGC CATTCGCCAG CTAAACC  27
```

( 2 ) INFORMATION FOR SEQ ID NO:17:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:17:

```
ATTGGATCCG GTTTAGCTGG CGAATGGC  28
```

( 2 ) INFORMATION FOR SEQ ID NO:18:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:18:

CCGAATTCTG TGAGGGTTCC AGGTGAC 27

( 2 ) INFORMATION FOR SEQ ID NO:19:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:19:

ATTGGATCCG TCACCTGGAA CCCTCACA 28

( 2 ) INFORMATION FOR SEQ ID NO:20:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:20:

CCGAATTCAT TACAGATCCT GGCCCA 26

( 2 ) INFORMATION FOR SEQ ID NO:21:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:21:

ACTGCCAATA CCAATATGTT CACATATGA 29

( 2 ) INFORMATION FOR SEQ ID NO:22:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:22:

CCCATAAACT CATGTTCTTG 20

( 2 ) INFORMATION FOR SEQ ID NO:23:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:23:

GGAGAAAATA TCCCATCACC 20

( 2 ) INFORMATION FOR SEQ ID NO:24:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:24:

CCGAATTCTG TAGAGGGTTC CAGGTGAC 28

( 2 ) INFORMATION FOR SEQ ID NO:25:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:25:

ATTGGATCCG GCATAGAAAG GGCCAA 26

HUMAN ISLET, HUMAN BRAIN AND MOUSE BRAIN GLUTAMIC ACID DECARBOXYLASE GAD POLYPEPTIDES

This is a continuation of application Ser. No. 07/839,805 filed on Feb. 21, 1992, now abandoned.

FIELD OF INVENTION

The present invention relates to the identification, cloning and sequencing of nucleic acid molecules encoding an isoform of the enzyme glutamic acid decarboxylase and further relates to the use of these molecules and/or peptides and polypeptides encoded thereby in diagnostic tests for Insulin Dependent Diabetes Mellitus and other diseases in which glutamic acid decarboxylase is an autoantigen and in the treatment of patients suffering from these diseases.

BACKGROUND TO THE INVENTION

The enzyme glutamic acid decarboxylase (hereinafter referred to as "GAD") catalyses the conversion of L-glutamic acid to the inhibitory neurotransmitter γ-amino butyric acid (hereinafter referred to as "GABA"). GAD is expressed both in the GABA secretory neurons of the central nervous system (1–3), in the β-cells of the pancreas (4,5), and in spermatoza (6). Analysis of imtmunoaffinity-purified, enzymatically active brain GAD has identified several isomeric forms of GAD with $M_r$ 54–67,000 (7,8). Using antisera raised to purified brain GAD to screen brain cDNA expression libraries, cDNAs encoding full length rat (9) and feline (10) GAD sequences have been isolated and sequenced. Comparisons of the deduced amino acid sequences of rat and feline GAD show that both proteins are 95% identical and, therefore, highly conserved during evolution.

Autoantibodies reactive with GAD in GABA-ergic neurons are present in the majority of sera from patients with the rare neurological disease Stiff Man Syndrome (hereinafter referred to "SMS"; 11,12). Patients positive for GAD autoantibodies have an increased frequency of polyendocrine autoimmunity especially Insulin Dependent Diabetes Mellitus (hereinafter referred to as "IDDM"). During the pre-clinical stage of IDDM and in patients with recent onset clinical IDDM, autoantibodies are frequently detected against an islet cell $M_r$ 64,000 protein designated "64K" (13). In a recent report, the 64K autoantigen was presumptively identified as GAD (14). However, Genovese (15) has suggested that GAD is co-precipitated with a separate 64K protein, the latter distinguished by tryptic products of $M_r$ 37,000/40,000 that are distinct from a $M_r$ 50,000 product of GAD. GAD comprises at least two isoforms encoded by separate genes (16, 17, 18). The predicted molecular weights of the known isoforms are approximately 67,000 and 65,000 (referred to as the "67K" and "65K" isoforms, respectively). The distribution of GAD isoforms in different tissues in still not well defined, but it is likely that the 65K isoform accounts for the GAD component of the 64K autoantigen (17).

In work leading up to the present invention, the inventors sought to clone the 67K isoform of GAD from human and other species for potential diagnostic and/or therapeutic use. In accordance with the present invention, human brain (HB), human pancreatic islet (HI) and mouse brain (MB) GAD (hereinafter referred to as "HBGAD", "HIGAD" and "MBGAD", respectively) have been cloned and sequenced. In further accordance with the present invention, recombinant GAD proteins corresponding to the 67K isoform and their fragments and derivatives were used as an antigen to detect antibodies and T-cells reactive with GAD thereby forming a basis for a new range of diagnostics and therapeutics for diseases of the type including preclinical and clinical IDDM and SMS and other diseases in which GAD is an autoantigen.

SUMMARY OF THE INVENTION

Accordingly, a first aspect of the present invention provides a nucleic acid molecule comprising a nucleotide sequence which encodes or is complementary to a sequence which encodes human or mouse glutamic acid decarboxylase (GAD) corresponding to a 67K isoform of the enzyme or antigenically active fragments or derivatives thereof.

Another aspect of the present invention provides a synthetic peptide or polypeptide displaying the antigenicity of all or a portion of the 67K isoform of GAD or a fragment thereof and reactive with autoantibodies and/or T-cells.

Yet another aspect of the present invention contemplates a method for the detection of antibodies to GAD in a sample which method comprises contacting a peptide or polypeptide corresponding to all or an antigenic portion of the 67K isoform of GAD with said sample for a time and under conditions sufficient for a complex to form between the peptide or polypeptide and an antibody reactive to GAD and then detecting the complex.

Still yet another aspect of the present invention provides a method for detecting diseases of the type including IDDM and SMS, or for screening asymptomatic individuals, by the detection and/or determination of the titre of autoantibodies in a biological sample from said individual, said method comprising contacting said sample with a peptide or polypeptide corresponding to all or an antigenic portion of the 67K isoform of GAD for a time and under conditions sufficient to form a complex between the peptide or polypeptide and an antibody reactive to GAD and then detecting the complex and/or the amount of peptide or polypeptide which has been bound in a complex Even yet another method of reducing autoantibodies and/or autoreactive T-cells to GAD in a patient in need thereof and/or to desensitise or induce tolerance to eliminate or diminish reactivity of autoreactive T-cells or autoantibodies to the autoantigen, said method comprising administering to said patient an effective amount of an antigenic peptide or polypeptide corresponding to all or part of the 67K isoform of GAD.

The present invention also provides a method of reducing autoantibodies and/or autoreactive T-celis to GAD in a patient in need thereof and/or to desensitise or induce tolerance to eliminate or diminish reactivity of autoreactive T-cells or autoantibodies to the autoantigen, said method comprising administering to said patient GAD reactive T-cell lines or clones or cell membranes and/or receptors for the antigen from said GAD reactive T-cell lines or clones for a time and under conditions sufficient to act as immunogens to induce inhibition and/or reduction of T-cell responses to GAD autoantigen.

BRIEF DESCRIPTION OF THE FIGURES

FIG. 1 shows a comparison of the DNA sequences corresponding to human brain GAD (HBGAD); SEQ ID NO.:1 and human islet GAD (HIGAD); SEQ ID NO.:2.

FIG. 2 shows the deduced amino acid sequences of HBGAD (SEQ ID NO.:3) and HIGAD (SEQ ID NO.:4) and their alignment with the equivalent region in the feline GAD (SEQ ID NO.:5) (amino acids 218–398).

FIG. 3 shows the nucleotide sequence and deduced amino acid sequence corresponding to the full length mouse brain GAD (MBGAD) (SEQ ID NO.:6).

FIG. 4 shows the nucleotide sequence and deduced amino acid sequence corresponding to the N-terminal fragment of MBGAD designated MBGAD12 (SEQ ID NO.:7) that encodes amino acids 1–204 of the published feline GAD sequence (10).

FIG. 5 shows the nucleotide sequence and deduced amino acid sequence corresponding to the mid-region fragment of MBGAD, designated MBGAD34 (SEQ ID NO.:8) corresponding to amino acids 198–404 of the published feline GAD sequence.

FIG. 6 shows the nucleotide sequence and deduced amino acid sequence corresponding to the C-terminal fragment of MBGAD, designated MBGAD56 (SEQ ID NO.:9) corresponding to amino acids 392–593 of the published feline GAD sequence.

FIG. 7 shows the full length nucleotide sequence and deduced amino acid sequence corresponding to human brain GAD (HBGAD-FL); (SEQ ID NO.:10).

FIG. 8 shows the nucleotide sequence and deduced amino acid sequence corresponding to the N-terminal fragment of HBGAD, designated HBGAD17 (SEQ ID NO.:11) corresponding to amino acids 1–250 of the published feline GAD sequence.

FIG. 9 shows the nucleotide sequence and deduced amino acid sequence corresponding to the mid region fragment of HBGAD or HIGAD, designated HBGAD14 or HIGAD14 (SEQ ID NO.:12) corresponding to amino acids 208–404 of the published feline GAD sequence.

FIG. 10 shows the nucleotide sequence and deduced amino acid sequence corresponding to the C-terminal region fragment of HBGAD, designated HBGAD65 (SEQ ID NO.:13), corresponding to amino acid 392–594 of the published feline GAD sequence.

FIG. 11 shows the full length nucleotide sequence and deduced amino acid sequence corresponding to human islet GAD (HIGAD-FL); (SEQ ID NO.:14).

DETAILED DESCRIPTION OF THE INVENTION

The present invention provides a nucleic acid molecule comprising a nucleotide sequence which encodes or is complementary to a sequence which encodes human or mouse glutamic acid decarboxylase (GAD) corresponding to a 67K isoform of the enzyme or antigenically active fragments or derivatives thereof.

By the "67K isoform" is meant the form of GAD having approximately $M_r$ 67,000 and/or any fragments, derivatives, homologues and/or immunological relatives thereof and which are distinguishable and/or otherwise distinct from the $M_r$ 65,000 form of GAD and which reacts preferentially to T-cells and/or autoantibodies from individuals with clinical or preclinical IDDM, SMS and/or other similar diseases.

Preferably, the GAD is human pancreatic islet GAD (HIGAD), human brain cell GAD (HBGAD) and/or mouse brain cell GAD (MBGAD). Preferably, the nucleic acid molecule is DNA, at least a part of which has a nucleotide sequence substantially corresponding to the sequence shown in FIGS. 1, 3, 7 and/or 11 or a fragment, derivative, homologue or or immunological relative thereof or one or more sequences complementary thereto. The present invention, however also extends to any single or multiple nucleotide substitutions, deletions and/or additions to the sequence shown in FIGS. 1, 3, 7 and/or 11 and which still encode a GAD or fragment or derivative thereof having the requisite antigenic profile and reactive with autoantibodies or T-cells. Furthermore, when the nucleic acid molecule is RNA, the ribonucleotide sequence will, in a preferred embodiment, be substantially complementary to one or more of the sequences shown in FIGS. 1, 3, 7 and/or 11 or a fragment, derivative, or homolgue thereof.

The present invention also provides a recombinant nucleic acid (e.g. DNA) molecule comprising a nucleotide sequence as described above operably linked to an expression control sequence. Such a recombinant molecule may, for example, comprise an expression vector. The present invention further extends to a host cell such as a bacterium, yeast, mammalian or insect cell transformed with such a recombinant molecule. A preferred mammalian cell line is the Chinese Hamster Ovary (CHO) cell line.

Another aspect of this invention is directed to a synthetic (e.g. recombinant) peptide or polypeptide displaying the antigenicity of all or a portion of an isoform of GAD which is reactive with autoantibodies and/or T-cells.

Such a synthetic peptide or polypeptide may, for example, be prepared by recombinant means such as by the expression of a host cell transformed with the recombinant molecules described above. The peptide or polypeptide may be fused to another peptide or polypeptide. Alternatively, it may be prepared by chemical synthesis, such as by the well-known Merrifield solid-phase synthesis procedure. The synthetic (eg. recombinant) peptide or polypeptide may or may not retain GAD enzymatic activity. Furthermore, although synthetic GAD or fragments thereof represent a preferred embodiment, the present invention also emends to biologically pure preparations of the naturally occurring enzyme or its fragrments. By "biologically pure" is meant a preparation of at least 60%, preferably at least 70%, more preferably at least 80% and still more preferably at least 90% by weight enzyme.

In a most preferred embodiment, the present invention extends to naturally occurring or synthetic peptide or polypeptides corresponding to MBGAD, HIGAD and/or HBGAD and to nucleotide sequences coding for same as well as to fragments, derivatives, homolgoues or immunological relatives thereof. By way of example, such fragments are shown in FIGS. 2, 4, 5, 6, 8, 9 and 10. By "derivatives" is meant to include any single or multiple amino acid substitution, deletion and/or addition relative to the naturally occurring sequence or to the sequence as shown in FIGS. 1, 3, 7 and/or 11 and including any single or multiple substitution, deletion and/or addition to other molecules associated with the peptide or polypeptide including carbohydrate lipid and/or other proteinacious moieties. Such derivatives, therefore, include glycosylated or non-glycosylated forms or molecules with altered glyclosylation patterns.

The present invention also contemplates a method for the detection of autoantibodies associated with IDDM which method comprises contacting a peptide or polypeptide corresponding to all, or an antigenic portion of, GAD, which GAD corresponds to the 67K isoform of the enzyme, or a fragment or derivative thereof with a biological sample from a patient to be tested for a time and under conditions sufficient for a complex to form between the peptide or polypeptide and an antibody reactive to GAD and then detecting the complex. Preferably, the biological sample is serum. Even more preferably, the peptide or polypeptide is immobilised onto a solid support before, during or after contact with the serum. Methods of detection are well known and include colorimetric, fluorometric and radioactive procedures.

Other detection means can also be used such as involving agglutination. This assay can be varied in any number of ways without departing from the scope of the present invention.

The present invention also extends to the use of a peptide or polypeptide corresponding to the 67K isoform of GAD, or antigenic fragments thereof, as an antigen in a diagnostic test for diseases of the type including IDDM and SMS, or for screening asymptomatic individuals by detection or determination of the titre of antibodies in a patient's serum, for example using ELISA or RIA technology or an agglutination assay using antigen-coated beads or the like.

This aspect of the present invention may conveniently be carried out by the detection and/or determination of the titre of autoantibodies in a biological sample (e.g. serum) from a human subject, said method comprising contacting said sample with a peptide or polypeptide corresponding to an antigenic portion of the 67K isoform of GAD or a fragment or derivative thereof for a time and under conditions sufficient for a complex to form between the peptide or polypeptide and an antibody reactive to GAD and then detecting the complex and/or amount of peptide or polypeptide which has been bound in the complex. Preferably, the peptide or polypeptide is immobilised onto a solid support before, during or after contact with the sample and the peptide or polypeptide is as hereinbefore defined.

Alternatively, such diseases may be detected or at least a negative result re-confirmed or otherwise by screening for GAD associated immune complexes. It is possible, for example, that a negative autoantibody result could have been caused by autoantibodies forming complexes with GAD thereby not being available for binding in the aforementioned assay. To conveniently detect GAD immune complexes, serun or other biological fluid is contacted with an anti-GAD antibody (e.g. a monoclonal antibody) for a time and under conditions sufficient for a GAD-autoantibody immune complex to bind.

Preferably, the anti-GAD antibody is first immobilised onto a solid support. An anti-immunoglobulin antibody, generally with a label or other reporter molecule attached, is then used to screen for the antibody component of the GAD complex.

One skilled in the art will immediately recognise that the assays as contemplated herein may be modified without departing from the scope of the present invention. All such modifications and variations of these assays are encompassed by the present invention.

The invention also extends to use of the peptides and/or polypeptides, or fragments, or derivatives of the present invention in the treatment of patients. In this later aspect, such methods of treatment include their use as an adsorbent to remove autoantibodies or autoreactive cells from a patient, their use in direct administration to a patient as a means of desensitising or inducing tolerance to eliminate or diminish reactivity of autoreactive T-cells or autoantibodies to the IDDM autoantigen or to generate T-cell lines or clones to be used for or as therapeutic agents.

As contemplated herein, the method of treatment includes but is not limited to the following examples of treatment. A first example of treatment is desensitisation or tolerance induction using an effective amount of GAD peptide or polypeptide or fragments thereof to alter T-cell recognition of GAD and induce T-cell suppression. This may be achieved by using the known effect of certain ultraviolet wavelengths, especially UV-B, to modify antigen presentation through the skin (see 19). Effective amounts of GAD peptide or polypeptide or fragments thereof would be applied epicutaneously to the skin of subjects exhibiting peripheral blood T-cell reactivity to GAD, after exposure of skin to UV-B radiation. Treatment would be repeated until such time that T-cell reactivity to GAD was suppressed. A second treatment involves application of GAD to the skin together with one or more cytokines such as but not limited to TNFα or β. A third treatment involves T-cell immunisation whereby T-cell lines are generated to GAD peptide or polypeptide or fragments thereof by standard procedures, calls attenuated by fixation with agents such as glutaraldehyde or paraformaldehyde, washed under sterile conditions and re-injected to patients for a time and under conditions causing suppression of the endogenous T-cell response to GAD. These approaches of treatment are applicable to the prevention of clinical IDDM in asymptomatic subjects with preclinical IDDM or subjects with recent onset clinical IDDM, as well as to the recurrence of IDDM in subjects who have received pancreas islet cell or insulin-producing cell transplants. These approaches are also applicable to SMS and other diseases where GAD is an autoantigen. In accordance with the present invention the effective amount of GAD peptide or polypeptide is 0.1 μg to 10 mg per dose and preferably 1.0 μg to 1 mg per dose. A dose may comprise a single administration or an administration protocol. Administration may be by any convenient means such as, but not limited to, intravenous, subcutaneous, epicutaneous, infusion, oral, topical, intranasal, supository or intraperitoneal administration. The GAD peptide or polypeptide may be administered alone or in combination with one or more other active molecules, molecules which facilitate the GAD peptide or polypeptide activity such as cytokines, and in particular, TNF-α and/or TNF-β.

In yet a further embodiment, the present invention contemplates the use of a peptide or polypeptide corresponding to the 67K isoform of GAD, or antigenic fragments or derivatives thereof, to measure reactivity of a patient's cells to the IDDM autoantigen. The peptide or polypeptide, or fragments or derivatives thereof, may be added, in solution or bound to a solid support together with cells from a patient derived from peripheral blood or from tissue biopsies either unfractionated, fractionated or derived as a continuous cell line. Reactivity to the autoantigen may then be measured by standard proliferation assays such as incorporation of tritiated thymidine, standard cytotoxic assays such as release of marker radioactivity from target cells, measurements of expressed or secreted molecules such as cytokines or other standard assays of cellular reactivity which are well known in the art.

In one embodiment of this aspect of this invention there is provided a diagnostic kit for assaying patient T-cells. Standard 96 well plates, as used in ELISA assays, are pre-coated with a monoclonal antibody (MAb) to a T-cell cytcokine such as γ-interferon (γ-IFN) with or without antigen. Alternatively, antigen is added in soluble form together with aliquots of peripheral blood mononuclear cells or T-cells. Incubation is allowed to proceed for two or more days, the cells are washed off, wells washed again and plates developed with a labelled second MAb to the cytokine such as anti-γ-FN conjugated with alkaline phosphatase or horseradish peroxidase. Colorimetric reaction and read-out systems can then be utilised. Alternatively, it is possible to visualise microscopically individual spots on bottoms of wells representing cytokine produced at the single T-cell level, thereby enabling the precursor frequency of antigen-reactive T-cells to be determined.

The present invention encompasses other forms of kits and diagnostic assays including a kit comprising a container adapted to contain a synthetic peptide or polypeptide corresponding to the 67 isoform of GAD or its fragments, derivatives, homologues and/or immunological relatives. The kit may contain a second container adapted to contain or receive a sample to be tested. A third container may be present adapted to contain reagents for detecting GAD-antibody complexes. Alternatively, where the kit is to detect GAD immune complexes, the kit may comprise one or more containers (e.g. wells) adapted to contain a GAD specific antibody (e.g. a monoclonal antibody). Additional containers with the kit may then contain recepticles for receiving fluid samples and a labelled antibody.

In further accordance with the present invention, expression of the cDNA insert encoding the GAD's described herein or fragments thereof, may be achieved in a number of different ways.

As an example, successful expression of the autoantigen as a fusion protein can be achieved using the pGEX vectors which give expression of glutathione S-transferase fusion proteins, using *E. coli* as the host cells. Expression could also be achieved, by way of example, using the well-known pEV vectors or the, polyhistidine expression vectors (23) again using *E. coli* as the host cells. Alternatively, GAD may be expressed as a non-fused polypeptide, by using appropriate vector and host cell combinations. Other vector and host cell combinations which can be used in accordance with the present invention including a number of well described yeast shuttle vectors for use in yeast cells, or eukaryotic vectors useful in continuous cell lines, (eg CHO cells) or transgenic animals.

The present invention will now be further described with reference to the following non-limiting Examples.

EXAMPLE 1

Materials and Methods

Mouse RNA. Mouse RNA was obtained from brains of BALB/C mice.

Humnan RNA. RNA was obtained from human adult brain and pancreatic islets. Islets were isolated from a donor pancreas by an intraductal collagenase distension procedure. Individually hand-picked islets were lysed in 5M guanidinium isothiocynate, 10 mM Tris pH 7.6, 10 mM EDTA and RNA purified by centrifugation through a 5.7M CsCl cushion. Total RNA from human brain was a gift of Claude Bernard from Latrobe University School of Behavioural Science, Australia.

Human cDNA libraries Two λgt-11 based human cDNA expression libraries were used as a source of GAD cDNA. A brain-stem cDNA library was purchased from Clonetech and the islet-cell library was a gift of Alan Permutt from the Washington School of Medicine, St. Louis. cDNA was prepared from phage stocks by a plate lysis method (20).

Polymease chain reaction (PCR). Based on the published rat (9) and feline (10) GAD cDNA sequences, oligonucleotide primers were designed from conserved regions. The primers used to isolate the various clones are shown in Table 1. First strand synthesis of total RNA (1 μg) was performed in 10 mM Tris pH 8.3, 50 mM KCl, 1.5 mM $MgCl_2$, 100 μM dNTPs (PCR buffer) containing 2 pmole of complimentary primer, 40 U of RNasin and 5 U of MoMLV reverse transcriptase at 37° C. for 30 min in a 50 μl reaction volume. λgt-11 cDNA (100 ng) or 10 μl of the first strand reaction was amplified in PCR buffer containing 20 pmole of each primer and 2.5 U of TaqI polymerase by 30 thermal cycles (one cycle: 1.5 min at 95° C.; 2.0 min at 37°–45° C.; 2.0 min at 72° C.). Reactions were analysed on low melting agarose gels and products of the expected size purified by phenol extraction (20).

Cloning and DNA sequencing. PCR amplified DNA fragments were cloned into the plasmid expression vector pGEX 1–3(21) and also into the histidine expression vector pDS56, (−1) and (−2) (23). Nucleotide sequence was determined by the dideoxy chain termination method (22) using the M13 universal primer and specific primers (RGAD 1, SEQ ID NO.: 15; RGAD2, SEQ ID NO.: 16; RGAD3, SEQ ID NO.: 17; RGAD4, SEQ ID NO.: 18; RGAD5, SEQ ID NO.: 19; RGAD6, SEQ ID NO.: 20; GAD1, SEQ ID NO.: 21; GAD5, SEQ ID NO.: 22; GAD7, SEQ ID NO.: 23) designed from internal GAD sequence, as described in Table 1.

TABLE 1

ORIGIN OF GAD cDNA CLONES

| GAD CLONE | AA REGION EQUIVALENT TO FELINE GAD | PCR SOURCE | OLIGONUCLEOTIDES 5'–3' |
|---|---|---|---|
| MBGAD 12 | 1–204 | BRAIN RNA | RGAD1 SEQ ID NO:15 ATTGGATCCACCGAGCTGATGGCGTCTTC<br>RGAD2 SEQ ID NO:16 CCGAATTCGCCATTCGCCAGCTAAACC |
| MBGAD34 | 198–404 | BRAIN RNA | RGAD3 SEQ ID NO:17 ATTGGATCCGGTTTAGCTGGCGAATGGC<br>RGAD4 SEQ ID NO:18 CCGAATTCTGTGAGGGTTCCAGGTGAC |
| MGAD56 | 392–593 | BRAIN RNA | RGAD5 SEQ ID NO:19 ATTGGATCCGTCACCTGGAACCCTCACA<br>RGAD6 SEQ ID NO:20 CCGAATTCATTACAGATCCTGGCCCA |
| HBGAD | 208–404 | BRAIN cDNA LIBRARY | GAD1 SEQ ID NO:21 ACTGCCAATACCAATATGTTCACATATGA<br>RGAD4 SEQ ID NO:22 CCCAATTCTGAGGGTTCCAGGTGAC |
| HIGAD | 208–404 | ISLET cDNA LIBRARY | GAD1 SEQ ID NO:21 ACTGCCAATACCAATATGTTCACATATGA<br>RGAD4 SEQ ID NO:23 CCGAATTCTCTGAGGGTTCCAGGTGAC |
| HBGAD17 | 1–250 | BRAIN RNA | RGAD1 SEQ ID NO:15 ATTGGATCCACCGAGCTGATGGCGTCTTC<br>GAD7 SEQ ID NO:23 GGAGAAAATATCCCATCACC |
| HBGAD14 | 208–404 | BRAIN RNA | GAD1 SEQ ID NO:21 ACTGCCAATACCAATATGTTCACATATGA<br>RGAD4 SEQ ID NO:18 CCGAATTCTGTGAGGGTTCCAGGTGAC |
| HBGAD65 | 392–594 | BRAIN RNA | GAD6 SEQ ID NO:25 ATTGGATCCGGCATAGAAAGGGCCAA<br>GAD5 SEQ ID NO:22 CCCATAAACTCATGTTCTTG |
| HBGAD-FL | 1–594 | BRAIN RNA | RGAD1 SEQ ID NO:15 ATTGGATCCACCGAGCTGATGGCGTCTTC |
| HIBAD-FL | 1–594 | PANCREAS RNA | GAD5 SEQ ID NO:22 CCCATAAACTCATGTTCTTG |

TABLE 1-continued

ORIGIN OF GAD cDNA CLONES

| GAD CLONE | AA REGION EQUIVALENT TO FELINE GAD | PCR SOURCE | OLIGONUCLEOTIDES 5'–3' |
|---|---|---|---|
| HIGAD14 | 208–404 | ISLET RNA | GAD1 SEQ ID NO:21 ACTGCCAATACCAATATGTTCACATATGA<br>RGAD4 SEQ ID NO:18 CCGAATTCTGTGAGGGTTCCAGGTGAC |

EXAMPLE 2

Cloning of Human GAD

To clone human GAD cDNA, oligonucleotide pairs overlapping nucleotide stretches conserved between rat and feline sequences were synthesised and used in PCR reactions to amplify cDNA extracted from brain and islet λt-11 expression libraries as well as from RNA extracted from human brain or human islets. In extensive PCR reactions using various combinations of oligonucleotide primers and temperatures of annealing, a product of 600 nucleotides was obtained from both brain and islet cDNA templates with the oligonucleotides primers:

- 5' ACTGCCAATACCAATATGTTCACATATGA 3' SEQ ID NO: 21 and
- 5' CCGAATTCTGTAGAGGGTTCCAGGTGAC 3' SEQ ID NO.:24) (complementary, contains an Eco RI site) which would correspond to nucleotide positions 739–768 and 1312–1330 of the published feline cDNA (10), respectively, representing the middle portion of the GAD open reading frame. The two 600 nucleotide PCR products were digested with EcoRI and SmaI ligated with pGEX-3X DNA cleaved with EcoRI and SmaI and transformed into *E. coli*. Restriction analysis of plasmid DNA from transformants identified a human brian GAD clone (HBGAD) and an islet GAD clone (HIGAD).

The 540 nucleotide DNA sequences determined for both HBGAD and HIGAD, excluding the oligonucleotide sequences, are shown in FIG. 1. These two sequences display 90% similarity with the feline GAD sequence and therefore, confirm the identity of the human clones. Alignment of the HBGAD sequence with the HIGAD sequence showed that they were identical except for four nucleotide changes at position 88 (T-A), 91(T-C) 128(C-T) and 366(C-T).

FIG. 2 shows the deduced amino acid sequences of HBGAD and HIGAD and their alignment with the corresponding region in the feline GAD protein (aa 218–393). The four nucleotide differences between HBGAD and HIGAD would result in three conservative amino acid changes at residues 247 (leucine→isoleucine) and 260 (threonine→isoleucine) and 248 (phenylalanine→leucine); residue 339 (leucine) remains unchanged because the nucleotide difference at position 366 is silent. These amino acid differences between the middle one-third of the brain and islet GAD proteins provide evidence for the existence of isomeric forms of GAD in human tissue.

Infiltration of the pancreatic islets with mononuclear cells culminates in the destruction of insulin-producing β cells and clinical IDDM (20). The enzyme GAD has recently been identified as a putative islet autoantigen in IDDM based on the ability of several IDDM sera to co-precipitate the 64K islet cell protein and GAD (14) and it has been shown that peripheral blood T cells from subjects with pre-clinical and clinical IDDM can be activated by islet membrane preparations containing the 64K autoantigen and GAD (24, 25). The finding of sequence differences between brain and islet GAD may now provide a genetic basis for selective autoimmune destruction of pancreatic islets.

EXAMPLE 3

Construction of a Full Length Human Brain and Islet GAD cDNA

Normal brain RNA was reverse-transcribed with either GAD 5 SEQ ID NO: 22 (5' CCCATAAACTCATGTTCTTG 3') or GAD 7 SEQ ID NO: 23 (5' GGAGAAAATATCCCATCACC 3') oligonucleotides. As shown in Table 1, amplification of the GAD7 and GAD5 first strand products by PCR using GAD specific oligonucleotides generated a cDNA encoding aa 1–250 HBGAD17 and an overlapping cDNA that encodes aa 208–594. One hundred nanograms of each fragment was denatured at 95° C. in PCR buffer and hybrid molecules extended and amplified using RGAD 1 and GAD 5 oligonucleotides that anneal at the end of the hybridised molecules (Table 1) to generate a full length human GAD clone that encodes the 594aa GAD open reading frame to generate a full length HBGAD and HIGAD (FIGS. 7 and 11).

EXAMPLE 4

Cloning of Mouse Brain GAD

Mouse Brain GAD was cloned as described above for HBGAD and HIGAD except that primers RGAD1 and RGAD6 (Table 1) were used.

EXAMPLE 5

T-Cell Responses to Recombinant Proteins 67 subjects were tested for their T-cell response to HBGAD and HIGAD.

Subject backgrounds were as follows:

- 15 Recent onset clinical Diabetics (less than 3 months after onset of symptoms)
- 44 Pre-clinical Diabetics (asymptomatic first degree relatives of a person with IDDM who are positive for islet cell antibodies that react with islets in frozen sections of human pancreas)
- 8 Controls (normal healthy young adults)

Peripheral blood mononuclear cells (PBMC) were separated by Ficoll Hypaque density gradient centrifugation, and washed twice. The cells were then resuspended ($2\times10^6$ /ml) in complete culture medium (RPMI 1640 with Hepes buffer 20 mM, penicillin 100 units/ml, streptomycin 100 μl/ml, $10^{-5}$M 2-mercaptoethanol and 5% autologous serum) and seeded (200 μl/well) into 96 well round-bottomed microtitre plates. The recombinant GAD fusion proteins HBGAD and HIGAD which contain the 196 amino acid middle portions of human brain and human islet GAD respectively, as described in Table 1 were added to final concentrations of 10, 1.0 and 0.1 μg/ml, together with glutathione-S-transferase (GST) to which the recombinant GAD antigen is fused. Sonicated fetal pig islets, which the present inventors have shown to contain GAD (24), as well as fetal pig liver, thyroid and kidney were also used as sources of antigen(s).

The cultures were incubated for 5 days in a humidified 5% $CO_2$ atmosphere with the addition of $^3$H-thymidine (1 μCi/well) for the last 17 hours. The cells were then harvested for scintillation counting. Median counts per minute (cpm) of each quadruplicate were used to derive stimulation indices, ie. cpm with antigen/cpm without antigen. A positive result was defined as a stimulation index greater than that obtained with GST (recombinant GAD proteins or greater than 2.0 (fetal tissues).

TABLE 2

Reactivity of Peripheral Blood T-cells

| Subject group | Antigens | | |
|---|---|---|---|
| | H islet GAD14 | H brain GAD14 | Fetal pig proislets |
| Recent onset clinical diabetes | 10/15 | 8/14 | 5/12 |
| Preclinical diabetes | 25/44 | 18/36 | 16/34 |
| Controls | 3/8 | 3/8 | 1/8 |

The results shown in Table 2 indicate that overall, 35/59 (59%) recent onset or preclinical subjects have circulating T-cells capable of proliferating in response to human islet GAD and (26/50) 52% to human brain GAD.

EXAMPLE 6

Antibody Responses to Recomnbinant Proteins

Sera samples from subjects were tested for an antibody response to the N-terminal fragment of recombinant murine brain GAD, MBGAD12 as well as against the full length recombinant human brain GAD.

Protein Used As Antigen

Recombinant mouse brain GAD12 was cloned and expressed as a fusion protein with glutathione-S-transferase (GST) in the pGEX system. MBGAD12 was cleaved with thrombin and the GAD portion affinity purified from GST using glutathione agarose beads. MBGAD34, MBGAD56, HBGAD17 and HBGAD65 were cloned and expressed as fusion proteins with six histidine residues at the N-terminus using the polyhistidine expression system.

ELISAS

In all ELISA assays, the recombinant GAD proteins, were coated at 1 μg/mL on plastic wells of a 96-well plate, wells were exposed to blocking buffer, washed and incubated with doubling dilutions of test sera, washed and exposed to alkaline phosphatase—conjugated second antibody, washed, developed with n-nitrophenol chromogen and read at 405 nM. An OD>mean+2 SD with control sera was taken as positive.

Subject Patients were as follows:

The results of ELISA using MBGAD12, MBGAD34 and MBGAD56, and HBGAD17 and HBGAD65 are shown in Tables 3 and 4, respectively:

TABLE 3

| | MBGAD12 | MBGAD34 | MBGAD56 |
|---|---|---|---|
| Preclinical IDDM | 5/9 | 5/9 | 4/9 |
| Recent onset Clinical IDDM | 2/13 | 4/13 | 3/13 |
| Controls | 0/22 | 0/20 | 0/20 |

Seven of nine (78%) preclinical IDDM and six of 13 (46%) recent-onset IDDM sera reacted with at least one of the MBGAD peptides. Only three of nine (33%) and one of 13 (8%) preclinical and recent onset IDDM sera, respectively, reacted with all three MBGAD fragments. None of the three GAD peptides was recognised preferentially by either sera group. These findings indicate that patterns of sera reactivity with recombinant MBGAD are heterogenous and that at least three major epitopes exist in the GAD67 isoform.

TABLE 4

| SUBJECTS | HBGAD 17 | HBGAD65 |
|---|---|---|
| Pre-clinical IDDM | 7/9 | 3/9 |
| Recent onset IDDM | 3/7 | 3/7 |
| Controls | 0/16 | 0/16 |

The results using the two human brain GAD fragments HBGAD17 and HBGAD65 in an ELISA format are comparable with those obtained using are equivalent mouse brain GAD peptides MBGAD12 and MBGAD56.

Those skilled in the art will appreciate that the invention described herein is susceptible to variations and modifications other than susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

REFERENCES

1. Roberts, E., Chase, T. N., and Tower, D. B. (1976) Kroc Foundation Series, Vol 5; GABA in Nervous System Function, Raven Press, New York.
2. Mugaini, E., and Oertel, W. H. (1985) In Handbook of Chemical Neuroanatomy (A. Bjorklund and T. Hokfelt, Eds.) Vol 4, pp 436–608 Elsevier, New York.
3. Blessing, W. W. (1990) Neuroscience 37, 171–185.
4. Okada, Y., Taniguchi. H., and Shimada, C. (1976) Science 194, 620–622.
5. Garry, D. J., Appel, N. M., Ganry, M. G., and Sorensen, R. L. (1988) J. Histochem. Cytochem. 36, 573–580.
6. Persson, H., Pelto-Huikko, M., Metsis, M., Soder, O., Brene, S., Skog, S., Hokfelt, T., and Ritzen, E. M. (1990) Mol. Cell. Biol. 19, 4701–4711.
7. Gottlieb, D. I., Chang, Y- C., and Schwob, J. E. 9186) Proc. Natl. Acad. Sci. USA. 83, 8808–8812.
8. Chang, Y- C., and Gottlieb, D. L. (1988) J. Neuroscience 8, 2123–2130.
9. Julien, J- F., Samana, P., and Mallet, J. (1990) J. Neurochemistry 54, 703–705.
10. Kobayashi, Y., Kaufman, D. L., and Tobin, A. J. (1987) J. Neuroscience 7, 2768–2772.
11. Solimena, M., Folli, F., Denis-Donini, S., Comi, G. C., Pozza, G., DeCamllli, P., and Vicari, A. M. (1988) N. Engl. J. Med. 318, 1012–1020.
12. Solimena, M., Folli, F., Aparisi, R., Pozza, G., and DeCamilli, P. (1990) N. Engl. J. Med. 322, 1555–1560.

13. Baekkeskov, S., Nielson, J. H. Marner, B., Bilde, T., Ludvigsson, J., and Lernmark, A. (1982) Nature 298, 167–169.

14. Baekkeskov, S., Aanstoot, H- J., Christgau, S., Reetz, A, Solimena, S., Cascalho, M., Folli, F., Richter-Olesen, H., and DeCamilli, P. (1990) Nature 347, 151–156.

15. Genovese, S., Cassidy, D., Bonifacio, E., Bottazzo, G. F. and Christie, M. R. (1991) Diab. Clin. Res. Prac. 14(Suppl 1), S11.

16. Cram, D. S., Barnett, L. D., Joseph, J. L. and Harrison, L. C. (1991) Biochem. Biophys. Res. Commun. 176, 1239–1244.

17. Karlsen, A. E., Hagopian, W. Z., Crubin, C. E. et el (1991) Proc. Nad. Acad. Sci. USA 88, 8337–8341.

18. Erlander, M. G., Tillakaratne, N. J. K., Feldblum, S., Patel, N. and Tobin, A. J. (1991) Neuron 7, 91–100.

19. Ullrich S. E., Yee, C. K., Kripke, M. L. (1986) Immunology 58, 158–190.

20. Sambrook, J., Fritsch, E. F., and Maniatis, T. (1989) In Molecular Cloning. A Laboratory Manual. Vol 1–3, Cold Spring Harbor Laboratory Press, Cold Spring Harbor, N.Y.

21. Smith, D. B., and Johnson, K. S. (1988) Gene 67, 31–40.

22. Sanger, F., Nicklen, S., and Coulson, A. R. (1977) Proc. Natl. Acad. Sci. USA. 74, 5463–5467.

23. Hochuli, E., Bamwarth, W., Dobeli, H., Gentz, R. and Stuber, D. (1988) Biotechnology 6 1321–1325.

24. Harison, L. C., De Aizpurua, H., Loudovaris, T., Campbell, I. L., Cebon, J. S., Tait, B. D., Colman, P. G. (1991) Diabetes 40,1128–1133.

25. Harrison, L. C., Chu, X. S., De Aizpurua, H. J., Graham, M., Honeyman, M. C., Colmnan, P. G. (1992) J. Clin. Invest. (in press).

What is claimed is:

1. A polypeptide having the amino acid sequence of SEQ ID NO:3.

2. A polypeptide consisting of the amino acid sequence of SEQ ID NO:3.

3. A polypeptide having the amino acid sequence of SEQ ID NO:4.

4. A polypeptide consisting of the amino acid sequence of SEQ ID NO:4.

5. A polypeptide having the amino acid sequence encoded by the nucleic acid sequence of SEQ ID NO:6.

6. A polypeptide consisting of the amino acid sequence encoded by the nucleic acid sequence of SEQ ID NO:6.

7. A polypeptide consisting of the polypeptide according to any one of claims 1, 3 or 5, and a contiguous second amino acid sequence.

8. A polypeptide according to claim 7 wherein said second amino acid sequence is glutathione-S-transferase (GST) or a portion thereof.

9. A polypeptide according to claim 7 wherein said second amino acid sequence comprises one or more histidine residues.

* * * * *

UNITED STATES PATENT AND TRADEMARK OFFICE
CERTIFICATE OF CORRECTION

PATENT NO. : 5,837,812
DATED : November 17, 1998
INVENTOR(S) : L. Harrison et al.

It is certified that error appears in the above-identified patent and that said Letters Patent is hereby corrected as shown below:

Title page,
Item [54], Title, "GAD" should read -- (GAD) --

Item [75] Inventors, "Honeyman" should read -- Honeymoon --

Item [21], Appl. No.: "308,952" should read -- 08/308,952 --

Item [56], References Cited, OTHER PUBLICATIONS, "Decarboxylae" should read -- Decarboxylase --

Column 8,
Line 1, "Humnan" should read -- Human --

Column 7 and 8,
Table 1, "RGAD4 SEQ ID NO.: 22" should read -- RGAD4 SEQ ID NO.: 18 --; and "RGAD4 SEQ ID NO.: 23" should read -- RGAD4 SEQ ID NO.: 18 --

Column 9,
Line 18, "λt-11" should read -- λgt-11 --

Column 12,
Line 50, REFERENCES, No 5: "Ganry" should read -- Garry --

Column 13,
Line 13, REFERENCES, No. 17: "et el" should read -- et al. --

Signed and Sealed this

Eighth Day of January, 2002

*Attest:*

JAMES E. ROGAN
*Director of the United States Patent and Trademark Office*

*Attesting Officer*